(12) United States Patent
Chen et al.

(10) Patent No.: US 11,445,968 B2
(45) Date of Patent: *Sep. 20, 2022

(54) QUANTITATIVE HEART TESTING

(71) Applicant: Heart Test Laboratories, Inc., Southlake, TX (US)

(72) Inventors: Guangren Chen, Shanghai (CN); David Krubsack, Allen, TX (US); Mark Hilz, Argyle, TX (US)

(73) Assignee: HEART TEST LABORATORIES, INC., Southlake, TX (US)

(*) Notice: Subject to any disclaimer, the term of this patent is extended or adjusted under 35 U.S.C. 154(b) by 188 days.

This patent is subject to a terminal disclaimer.

(21) Appl. No.: 16/739,439

(22) Filed: Jan. 10, 2020

(65) Prior Publication Data

US 2020/0146574 A1 May 14, 2020

Related U.S. Application Data

(60) Continuation of application No. 15/644,644, filed on Jul. 7, 2017, now Pat. No. 10,561,327, which is a
(Continued)

(51) Int. Cl.
*A61B 5/00* (2006.01)
*A61B 5/339* (2021.01)
(Continued)

(52) U.S. Cl.
CPC ............ *A61B 5/339* (2021.01); *A61B 5/0006* (2013.01); *A61B 5/25* (2021.01); *A61B 5/316* (2021.01);
(Continued)

(58) Field of Classification Search
CPC ... A61B 5/726; A61B 5/0452; A61B 5/04012; A61B 5/0402; A61B 5/0006;
(Continued)

(56) References Cited

U.S. PATENT DOCUMENTS 4,333,475 A 6/1982 Moreno et al.
5,109,862 A 5/1992 Kelen et al.
(Continued)

FOREIGN PATENT DOCUMENTS

AU 2016332207 8/2021
CN 1539372 10/2004
(Continued)

OTHER PUBLICATIONS

"U.S. Appl. No. 15/271,155, Examiner Interview Summary dated Mar. 14, 2017", 3 pgs.
(Continued)

*Primary Examiner* — Deborah L Malamud
(74) *Attorney, Agent, or Firm* — Schwegman Lundberg & Woessner, P.A.

(57) ABSTRACT

Heart condition and function can be quantified using repolarization measures and/or repolarization indices derived from a time-frequency transform of an electrocardiogram, e.g., based on points in time associated with the T wave. The electrocardiograms, time-frequency maps derived therefrom, and/or indices obtained by analysis of the time-frequency maps and electrocardiograms may be assembled into a user interface. Further embodiments are described.

20 Claims, 14 Drawing Sheets

Related U.S. Application Data division of application No. 15/271,155, filed on Sep. 20, 2016, now Pat. No. 9,700,226.

(60) Provisional application No. 62/321,856, filed on Apr. 13, 2016, provisional application No. 62/276,639, filed on Jan. 8, 2016, provisional application No. 62/276,596, filed on Jan. 8, 2016, provisional application No. 62/235,309, filed on Sep. 30, 2015.

(51) Int. Cl.

| | | |
|---|---|---|
| *A61B 5/25* | (2021.01) | |
| *A61B 5/316* | (2021.01) | |
| *A61B 5/318* | (2021.01) | |
| *A61B 5/349* | (2021.01) | |
| *A61B 5/352* | (2021.01) | |

(52) U.S. Cl.
CPC ............. *A61B 5/318* (2021.01); *A61B 5/349* (2021.01); *A61B 5/352* (2021.01); *A61B 5/7253* (2013.01); *A61B 5/743* (2013.01); *A61B 5/7435* (2013.01); *A61B 5/726* (2013.01)

(58) Field of Classification Search
CPC ... A61B 5/0245; A61B 5/7257; A61B 5/7271; A61B 5/02; A61B 5/04; A61B 5/72; A61B 5/7235; A61B 5/7246; A61B 5/7253; A61B 5/7282; A61B 5/7285; G06F 19/345; G06F 17/14; A61N 1/08; A61N 1/3702; A61N 1/365; A61N 1/37; G06Q 50/22
See application file for complete search history.

(56) References Cited

U.S. PATENT DOCUMENTS

| | | | |
|---|---|---|---|
| 5,797,840 | A | 8/1998 | Akselrod et al. |
| 5,827,195 | A | 10/1998 | Lander |
| 5,842,997 | A | 12/1998 | Verrier et al. |
| 5,935,082 | A | 8/1999 | Albrecht et al. |
| 6,148,228 | A | 11/2000 | Fang et al. |
| 6,438,419 | B1 | 8/2002 | Callaway et al. |
| 7,676,264 | B1 | 3/2010 | Pillai et al. |
| 8,478,393 | B2 | 7/2013 | Ramanathan et al. |
| 8,849,386 | B2 | 9/2014 | Waters |
| 9,050,007 | B1 | 6/2015 | Brockway et al. |
| 9,700,226 | B2 | 7/2017 | Krubsack et al. |
| 10,561,327 | B2 | 2/2020 | Chen et al. |
| 2005/0234357 | A1 | 10/2005 | Xue et al. |
| 2006/0058694 | A1 | 3/2006 | Clark et al. |
| 2006/0122526 | A1 | 6/2006 | Berenfeld et al. |
| 2006/0287605 | A1 | 12/2006 | Lin et al. |
| 2008/0109041 | A1 | 5/2008 | De Voir |
| 2008/0255465 | A1 | 10/2008 | Nelson |
| 2010/0152598 | A1 | 6/2010 | Zhang |
| 2010/0317981 | A1 | 12/2010 | Grunwald |
| 2011/0092838 | A1 | 4/2011 | Helfenbein et al. |
| 2011/0282227 | A1 | 11/2011 | Zhang |
| 2012/0053476 | A1 | 3/2012 | Hopenfeld |
| 2012/0123232 | A1 | 5/2012 | Najarian et al. |
| 2013/0035738 | A1 | 2/2013 | Karst et al. |
| 2013/0172723 | A1 | 7/2013 | Baxi et al. |
| 2013/0261482 | A1 | 10/2013 | Marziliano et al. |
| 2013/0296726 | A1 | 11/2013 | Niebauer et al. |
| 2014/0148718 | A1 | 5/2014 | Stickney et al. |
| 2014/0323900 | A1 | 10/2014 | Bibian et al. |
| 2014/0371807 | A1 | 12/2014 | Ghosh et al. |
| 2015/0208931 | A1 | 7/2015 | Kasamsook et al. |
| 2016/0143543 | A1 | 5/2016 | Zhang |
| 2017/0086693 | A1 | 3/2017 | Peterson et al. |
| 2017/0086696 | A1 | 3/2017 | Chen et al. |
| 2017/0196473 | A1 | 7/2017 | Krubsack et al. |
| 2017/0303806 | A1 | 10/2017 | Chen et al. |

FOREIGN PATENT DOCUMENTS

| | | |
|---|---|---|
| CN | 101011242 | 8/2007 |
| CN | 101049235 | 10/2007 |
| CN | 101642368 | 2/2010 |
| CN | 102512152 | 6/2012 |
| CN | 103857330 | 6/2014 |
| CN | 104382590 | 3/2015 |
| CN | 104640498 | 5/2015 |
| CN | 104736049 | 6/2015 |
| CN | 108471942 A | 8/2018 |
| CN | 108471942 | 10/2021 |
| IN | 201817014481 A | 9/2018 |
| JP | 2001218747 A | 8/2001 |
| JP | 2010538802 A | 12/2010 |
| JP | 2012508079 A | 4/2012 |
| JP | 2012106004 A | 6/2012 |
| RU | 2374986 C1 | 12/2009 |
| RU | 2512931 C2 | 4/2014 |
| WO | WO-2004086967 A1 | 10/2004 |
| WO | WO-2005096170 A1 | 10/2005 |
| WO | 2006008743 | 1/2006 |
| WO | WO-2010000009 A1 | 1/2010 |
| WO | WO-2012119665 A1 | 9/2012 |
| WO | WO-2013106559 A2 | 7/2013 |
| WO | WO-2017058578 A1 | 4/2017 |

OTHER PUBLICATIONS

"U.S. Appl. No. 15/271,155, Examiner Interview Summary dated Apr. 13, 2017", 3 pgs.

"U.S. Appl. No. 15/271,155, Non Final Office Action dated Mar. 31, 2017", 7 pgs.

"U.S. Appl. No. 15/271,155, Non Final Office Action dated Dec. 23, 2016", 10 pgs.

"U.S. Appl. No. 15/271,155, Notice of Allowance dated May 22, 2017", 7 pgs.

"U.S. Appl. No. 15/271,155, Response filed Mar. 23, 2017 to Non Final Office Action dated Dec. 23, 2016", 15 pgs.

"U.S. Appl. No. 15/271,155, Response filed Apr. 13, 2017 to Non Final Office Action dated Mar. 31, 2017", 10 pgs.

"U.S. Appl. No. 15/271,155, Restriction Requirement dated Nov. 14, 2016", 8 pgs.

"U.S. Appl. No. 15/271,160, Examiner Interview Summary dated Apr. 13, 2017".

"U.S. Appl. No. 15/271,160, Examiner Interview Summary dated Oct. 13, 2017", 3 pgs.

"U.S. Appl. No. 15/271,160, Final Office Action dated Aug. 4, 2017", 17 pgs.

"U.S. Appl. No. 15/271,160, Non-Final Office Action dated Jan. 17, 2017", 16 pgs.

"U.S. Appl. No. 15/271,160, Response filed Apr. 13, 2017 to Non-Final Office Action dated Jan. 17, 2017", 12 pgs.

"U.S. Appl. No. 15/271,160, Response filed Dec. 14, 2016 to Restriction Requirement dated Nov. 10, 2016", 3 pgs.

"U.S. Appl. No. 15/271,160, Restriction Requirement dated Nov. 10, 2016", 6 pgs.

"U.S. Appl. No. 15/400,527, Non Final Office Action dated Nov. 19, 2018", 13 pgs.

"U.S. Appl. No. 15/644,644, Final Office Action dated May 16, 2019", 8 pgs.

"U.S. Appl. No. 15/644,644, Non Final Office Action dated Dec. 4, 2018", 9 pgs.

"U.S. Appl. No. 15/644,644, Notice of Allowance dated Oct. 11, 2019", 7 pgs.

"U.S. Appl. No. 15/644,644, Response filed May 3, 2019 to Non Final Office Action dated Dec. 4, 2018", 11 pgs.

"U.S. Appl. No. 15/644,644, Response filed Sep. 16, 2019 to Final Office Action dated May 16, 2019", 8 pgs.

(56) References Cited

OTHER PUBLICATIONS

"European Application Serial No. 16852320.7, Extended European Search Report dated Aug. 28, 2018", 10 pgs.

"International Application Serial No. PCT/US2016/052717, International Preliminary Report on Patentability dated Apr. 12, 2018", 12 pgs.

"International Application Serial No. PCT/US2016/052717, International Search Report dated Dec. 9, 2016", 3 pgs.

"International Application Serial No. PCT/US2016/052717, Written Opinion dated Dec. 9, 2016", 10 pgs.

"Japanese Application Serial No. 2018-517322, Notification of Reasons for Rejection dated Apr. 23, 2019", w/English Translation, 6 pgs.

"Japanese Application Serial No. 2018-517322, Response filed Jul. 22, 2019 to Notification of Reasons for Rejection dated Apr. 23, 2019", w/English Claims, 10 pgs.

"Russian Application Serial No. 2018115833, Office Action dated Feb. 21, 2019", w/English Translation, 29 pgs.

Addison, Paul S., "Wavelet transforms and the ECG: a review", Institute of Physics Publishing Physiol. Meas. 26, (2005), R155-R199.

Barmase, Swapnil, et al., "Wavelet Transform-Based Analysis of QRS complex in ECG Signals", Indian Institute of Science Education and Research, Kolkata, Mohanpur campus, Nadia 741252, 7 pgs.

Bialasiewicz, Jan T, "Application of Wavelet Scalogram and Coscalogram for Analysis of Biomedical Signals", Proceeding of the World Congress on Electrical Engineering and Computer Systems and Science(EECSS 2015), Papar No. 333, (Jul. 13, 2015), 8 pgs.

El-Sherif, Nabil, et al., "Definition of the Best Prediction Criteria of the Time Domain Signal-averaged Electrocardiogram for Serious Arrhythmic Events in the Postinfarction Period", JACC vol. 25, No. 4, (1995), 908-914.

Heathers, James AJ, "Smartphone-enabled Pulse Rate Variability: an Alternative Methodology for the Collection of Heart Rate Variability in Psychophysiological Research", International Journal of Psychophysiology; 89(3), (2013), 8 pgs.

Jarrin, Denise C., et al., "Measurement Fidelity of Heart Rate Variability Signal Processing: the Devil is in the Details", International Journal of Psychophysiology; 86(1):, (2012), 88-97.

Lemire, D., et al., "Wavelet Time Entropy, T wave morphology and myocardial ischemia", IEEE Transactions in Biomedical Engineering, vol. 47, No. 7, (Jul. 2000), 11 pgs.

Li, C, et al., "Detection of ECG Characteristic Points Using Wavelet Transforms", IEEE Transactions on Biomedical Engineering, IEEE Service Center, Piscataway, NJ, USA, vol. 42, No. 1,(Jan. 1, 1995), 21-28.

Schlegel, Todd T., "Real-time 12-lead High-frequency Qrs Electrocardiography for Enhanced Detection of Myocardial Ischemia and Coronary Artery Disease", Mayo Clinic Proceedings; 79(3), (2004), 339-350.

Xiankui, Wan, et al., "An ECG T waves detection scheme based on the compensatory criterion", Biomedical Engineering and Informatics (BMEI), 2010 3rd International Conference on, IEEE, Piscataway, NJ, USA, (Oct. 16, 2010), 730-734.

Zhong, J., et al., "The Ecg Recording and Analysis Instrumentation Based on Virtual Instrument Technology and Continuous Wavelet Transform", Proceedings of the 25th Annual International Conference of the IEEE; 4:, (2003), 3176-3179.

"Brazilian Application Serial No. BR112018005982-0, Office Action dated Jul. 3, 2020", w/ English Translation, 5 pgs.

"Chinese Application Serial No. 201680069952.6, Office Action dated Aug. 24, 2020", w/ English Translation, 32 pgs.

"Australian Application Serial No. 2016332207, First Examination Report dated Aug. 28, 2020", 5 pgs.

"Brazilian Application Serial No. BR112018005982-0, Response filed Oct. 9, 2020 to Office Action dated Jul. 3, 2020", w/o English Translation, 76 pgs.

U.S. Appl. No. 15/271,155, U.S. Pat. No. 9,700,226, filed Sep. 20, 2016, Quantitative Heart Testing.

U.S. Appl. No. 15/644,644, filed Jul. 7, 2017, Quantitative Heart Testing.

U.S. Appl. No. 15/400,527, filed Jan. 6, 2017, Quantitative Heart Monitoring and Diagnostics.

U.S. Appl. No. 15/271,160, filed Sep. 20, 2016, User Interfaces for Heart Test Devices.

"Israel Application Serial No. 258358, Office Action dated Jan. 24, 2021", with English translation, 6 pages.

"Chinese Application Serial No. 201680069952.6, Response filed Feb. 10, 2021 to Office Action dated Aug. 24, 2020", with English claims, 34 pages.

"Chinese Application Serial No. 201680069952.6, Office Action dated May 12, 2021", with English translation, 12 pages.

"Indian Application Serial No. 201817014481, First Examination Report dated May 27, 2021", with English translation, 10 pages.

"Australian Application Serial No. 2016332207, Response filed Jul. 6, 2021 to First Examination Report dated Aug. 28, 2020", 14 pgs.

"Chinese Application Serial No. 201680069952.6, Response filed Jul. 14, 2021 to Office Action dated May 12, 2021", with English claims, 21 pages.

"Israel Application Serial No. 258358, Response filed Sep. 29, 2021 to Office Action dated Jan. 24, 2021", with English claims, 4 pages.

Martis, "Current Methods in Electrocardiogram Characterization", Computers in Biology and Medicine, (May 1, 2014), pp. 133-149.

Zeraatkar, "Arrhythmia Detection based on Morphological and Time-frequency Features of T-wave in Electrocardiogram", Journal of medical signals and sensors, (May 31, 2011), pp. 99-106.

QUANTITATIVE HEART TESTING

CROSS-REFERENCE TO RELATED APPLICATIONS

This application is a continuation of U.S. application Ser. No. 15/644,644, filed on Jul. 7, 2017, which is a divisional of U.S. application Ser. No. 15/271,155, filed on Sep. 20, 2016, which claims priority to and the benefit of U.S. Provisional Application No. 62/235,309, filed on Sep. 30, 2015, U.S. Provisional Application No. 62/276,596, filed on Jan. 8, 2016, U.S. Provisional Application No. 62/276,639, filed on Jan. 8, 2016, and U.S. Provisional Application No. 62/321,856, filed on Apr. 13, 2016. The disclosures of priority applications are hereby incorporated herein by reference.

TECHNICAL FIELD

The present disclosure relates generally to heart testing, and more particularly to systems, devices, and methods for quantifying and/or visualizing heart condition.

BACKGROUND

Heart testing for coronary heart disease, myocardial ischemia, and other abnormal heart conditions is routinely performed using an electrocardiogram (ECG), which represents electrical potentials reflecting the electrical activity of the heart measured via electrodes placed on the patient's skin. The heart's electrical system controls timing of the heartbeat by sending an electrical signal through the cells of the heart. The heart includes conducting cells for carrying the heart's electrical signal, and muscle cells that contract the chambers of the heart as triggered by the heart's electrical signal. The electrical signal starts in a group of cells at the top of the heart called the sinoatrial (SA) node. The signal then travels down through the heart, conducting cell to conducting cell, triggering first the two atria and then the two ventricles. Simplified, each heartbeat occurs by the SA node sending out an electrical impulse. The impulse travels through the upper heart chambers, called "atria", electrically depolarizing the atria and causing them to contract. The atrioventricular (AV) node of the heart, located on the interatrial septum close to the tricuspid valve, sends an impulse into the lower chambers of the heart, called "ventricles," via the His-Purkinje system, causing depolarization and contraction of the ventricles. Following the subsequent repolarization of the ventricles, the SA node sends another signal to the atria to contract, restarting the cycle. This pattern and variations therein indicative of disease are detectable in an ECG, and allow medically trained personnel to draw inferences about the heart's condition. However, not every developing abnormality is immediately visible in an ECG, and, consequently, many patients are misdiagnosed as healthy. Furthermore, although ECGs are nowadays typically recorded and displayed electronically, they often go little beyond the printed ECG traces of the past in the type of information they provide and the intuitiveness and convenience with which such information is presented.

DESCRIPTION

Figure 1:
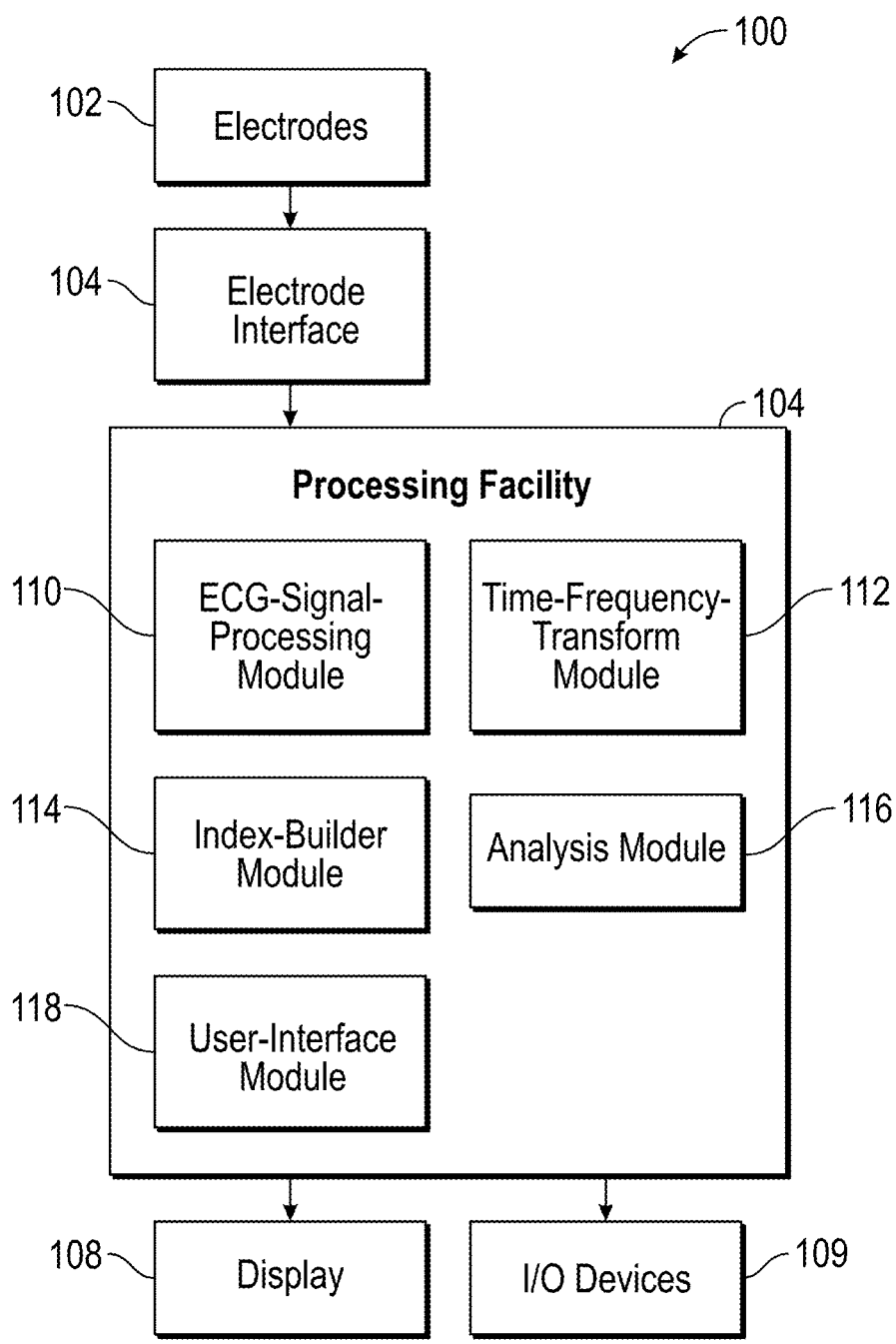
FIG. 1 is a block diagram illustrating an example system for quantifying and visualizing heart condition in accordance with various embodiments.

Described herein, in various embodiments, are systems, devices, and methods for enhancing the diagnostic capabilities and utility of ECGs through advanced signal processing and through the presentation of data in a meaningful, user-friendly way.

In accordance with various embodiments, ECGs—i.e., time-domain signals reflecting the electric potential of the heart throughout one or more cardiac cycles—are computationally converted, by a suitable time-frequency transform, into respective two-dimensional time-frequency maps. In a "time-frequency map," as the term is herein broadly understood, the signal value (corresponding, e.g., to a measured electric potential) is provided as a function of two independent variables: time, and a measure of the spectral components of the signal such as, e.g., frequency (in the narrower sense) or a scaling factor. For example, in some embodiments, short-time Fourier transform is used to convert the ECGs into spectrograms, where the signal value is a function of time and frequency. In other embodiments, the ECGs are converted by (continuous or discrete) wavelet transform into so-called scalograms, where the signal value is a function of time and a scaling factor. More generally, a filter bank may be used to transform the ECG into a time-frequency representation. For ease of reference, the dimension of the time-frequency map that corresponds to the frequency or scaling factor (or any other measure of the spectral components) is herein generally referred to as the frequency dimension or simply frequency.

The time-frequency maps, by themselves or in conjunction with the ECGs from which they are derived, may be displayed to a physician (or other clinical personnel) for interpretation, and/or analyzed automatically to derive quantitative metrics of heart condition and function therefrom. By spreading out the spectral components of the measured ECG signals, the time-frequency maps can visualize information not discernible from the ECGs themselves, which can help detect conditions traditionally not diagnosed based on ECGs, such as, e.g., myocardial ischemia.

It has been found that the signal portion associated with the T wave within the ECG, which represents the repolarization of the ventricles, is a particularly suitable indicator of heart condition. Accordingly, in various embodiments, repolarization measures associated with one or more points in time (or ranges in time) within the T wave are determined. More specifically, in some embodiments, the T wave, and one or more relevant points in time therein, are identified within an ECG, and the time-frequency map derived from the ECG is then analyzed at the one or more points in time to determine one or more extrema (i.e., maxima or minima) of the signal value of the time-frequency map across frequency. (The phrase "across frequency," in this context, means that the maximum or minimum is determined for a fixed point in time from the signal value of the time-frequency map as a (one-dimensional) function of frequency only. By contrast, an extremum determined "across time and frequency" is the maximum or minimum signal value within the two-dimensional time-frequency map (or a two-dimensional portion thereof, e.g., if the time dimension is limited to an interval).) In certain embodiments, repolarization measures are determined for the point in time where the T wave peaks (i.e., assumes its maximum), and/or for "early" and/or "late" points in time within the T wave, that is, for points in time preceding and/or following the maximum of the T wave and being in the vicinity of that maximum (e.g., points falling within a time interval defined by two points bracketing the T wave maximum at which the T wave assumes half its maximum value). In certain embodiments, the early and late times are selected as close as possible to the peak while still being distinguishable. A "repolarization peak measure (RPM)," a "repolarization early measure (REM)," and a "repolarization late measure (RLM)" are defined herein as the maximum or minimum signal value of the time-frequency map at the time where the T wave peaks, the early time, and the late time, respectively.

From one or more repolarization measures (e.g., corresponding to extrema across frequency at various points in time associated with the T wave) determined for a patient, one or more repolarization indices may be computed. For example, repolarization measures (such as, e.g., REMs, RLMs, and/or RPMs) may be determined from time-frequency maps computed from the ECGs of different leads (signals acquired by different electrodes or combinations thereof), and may be averaged across multiple leads, multiple cardiac cycles within each time-frequency map, or both. Left and right ventricular repolarization indices, indicative of the condition of the left or right ventricles of the heart, may be derived from one or more repolarization measures associated with leads associated with the left and right ventricle, respectively, optionally in conjunction with age- and/or gender-dependent adjustment factors and/or a measured heart rate. The repolarization indices may be displayed or otherwise communicated to a physician (or other clinically trained person) to facilitate an assessment of the ventricles' condition, or may be output to an automatic diagnosis algorithm. In some embodiments, repolarization measures or repolarization indices are compared against each other, or against a threshold, to assess whether, and/or to which degree, heart function is impaired. For example, an RLM exceeding an REM, a right ventricular repolarization index exceeding a left ventricular repolarization index, or an RLM or REM falling below a specified threshold may all indicate an abnormality in heart function.

The overall signal level in ECGs, and consequently also the time-frequency maps derived therefrom, can show significant variations between measurements (e.g., taken at different times) and between leads within a measurement that are unrelated to the heart's condition and function and, thus, do usually not possess clinical significance. Therefore, to render the data (including ECGs, time-frequency maps, repolarization measures, and repolarization indices) comparable across measurements, leads, or even patients, the time-frequency map is normalized, in various embodiments, prior to display and/or to the determination of the repolarization measures. Normalization may be applied to the signed time-frequency map as it results directly from time-frequency transform, that is, a time-frequency map generally having both positive and negative signal values, or to the unsigned time-frequency map as it results by taking the absolute value of the time-frequency transform. Further, the normalization may be uniformly applied to the entire time-frequency map, or separately to different portions thereof (e.g., portions corresponding to individual heartbeats.) The normalization may be based on the difference between the maximum and the minimum of the time-frequency map (in its entirety) or a portion thereof (e.g., a portion limited, in the time dimension, to a time interval corresponding to an integer number of heartbeats, a single heartbeat, or even only a segment of the ECG signal within a heartbeat). For example, the time-frequency map may be shifted up in signal value by the negative of its minimum value (such that the minimum of the shifted map equals zero), and thereafter scaled based on the (new) maximum value. Typically, the maximum of the time-frequency transform corresponds to the R peak or the S peak within the QRS complex (which are not always clearly identifiable in each lead), but maxima falling outside the time interval corresponding to the QRS complex are also possible. In various embodiments, the portion of the time-frequency map across which a maximum and minimum for normalization are identified is chosen to encompass at least the RS segment.

In accordance with various embodiments, the ECGs, time-frequency maps, and/or repolarization indices resulting from heart testing are assembled into a user interface for display to, e.g., a physician. The time-frequency maps may be shown as color maps (which, if based on normalized signal values, may each span the full color range from red to blue). Since, in general, not all ECGs and associated time-frequency maps always fit simultaneously within the display of the heart test device, the user interface may provide user-input control elements that allow an operator to select the leads for which ECGs and/or time-frequency maps are to be displayed, and in which order. The user interface may further enable the operator to scroll through all available leads and, within the ECG and/or time-frequency map for a given lead, to scroll along the time axis to different portions; in some embodiments, such scrolling can be accomplished via a swiping gesture on a touchscreen display. During scrolling along the time axis, an ECG and its corresponding time-frequency map may be locked so as to both display the same limited time range. In some embodiments, the user interface further displays a Glasgow-analysis summary (as known to those of ordinary skill in the art), and/or a graphic icon generated based on the numerical repolarization indices to provide an intuitive visual indicator of overall heart condition. The icon may, for instance, be or include a segmented waveform symbol that signifies, via a number of greyed-out segments within an otherwise colored symbol, a degree of impairment of heart function (e.g., whether the heart condition is normal, abnormal, or suspect). The results of ECG testing may be displayed within a report screen of a multiple-screen user interface configured to guide clinical personnel through the electrocardiography process, from patient selection and connection of the patient electrodes through the performance of an electrocardiography test to the presentation of the test results.

The foregoing will be more readily understood from the following more detailed description, which references the accompanying drawings.

FIG. 1 illustrates, in block-diagram form, various functional components of an example system for quantifying and visualization heart condition in accordance with various embodiments. The system 100 includes one or more electrodes 102 for acquiring ECG signals (e.g., 10 electrodes for a traditional 12-lead ECG), a processing facility 104 for processing the ECG signals, e.g., to obtain time-frequency maps and repolarization indices, and an electrode interface 106 connecting the electrodes 102 to the processing facility 104. The electrode interface 106 includes circuitry that outputs electrical signals suitable as input to the processing facility 104, e.g., by digitally sampling analog input signals. The system 100 further includes a display device 108 for outputting the ECG test results (including, e.g., the ECGs, time-frequency maps, and/or repolarization indices), and optionally other input/output devices 109, such as a keyboard and mouse and/or a printer, for instance. The display device 108 may be a touchscreen doubling as a user-input device. The processing facility 104, electrode interface 106, display 108, and input/output devices 109 may be implemented as a single, stand-alone device implementing all computational functionality for ECG signal processing and presentation. Alternatively, they may be provided by the combination of multiple communicatively coupled devices. For example, an ECG test device with limited functionality for recording and/or processing ECG signals received from one or more electrodes 102 via an electrode interface 106 of the device may outsource certain computationally intense processing tasks to other computers with which it is communicatively coupled via a wired or wireless network. Thus, the functionality of the processing facility 104 may be distributed between multiple computational devices that communicate with each other. Whether provided in a single device or distributed, the processing facility 104 may be implemented with dedicated, special-purpose circuitry (such as, e.g., a digital signal processor (DSP), field-programmable gate array (FPGA), analog circuitry, or other), a suitably programmed general-purpose computer (including at least one processor and associated memory), or a combination of both.

The processing facility 104 may include various functionally distinct modules, such as an ECG-signal-processing module 110 that prepares the (e.g., digitally sampled) electrical potentials for display (e.g., by filtering, smoothing, scaling, etc.) and analysis; a time-frequency transform module 112 that converts each ECG signal into a two-dimensional time-frequency map (signed or unsigned) and, optionally, normalizes the time-frequency map; an index-builder module 114 that analyzes the ECGs and/or time-frequency maps to determine repolarization measures and/or repolarization indices (which may involve, e.g., identifying delimiters between successive cardiac cycles, determining certain features (such as the QRS complex, T wave, and other segments) within the ECGs, selecting points in time within the T wave, determining repolarization measures (such as, e.g., REMs, RLMs, and/or RPMs) from the time-frequency maps, reading in any other relevant parameters (such as gender- or age-based adjustment factors, heart rate, etc.), and computing the ventricular indices and/or any functions thereof); an analysis module 116 that derives further metrics and/or determines heart condition from the repolarization indices; and a user-interface 118 module that generates graphic representations of the data provided by the other modules and assembles them into a screen for display. The ECG-signal-processing module 110 may be a conventional processing module as used in commercially available heart monitors and/or as is capable of straightforward implementation by one of ordinary skill in the art. The time-frequency transform module 112, index-builder module 114, analysis module 116, and user-interface module 118 implement algorithms and provide functionality explained in detail below, and can be readily implemented by one of ordinary skill in the art given the benefit of the present disclosure.

As will be readily appreciated, the depicted modules reflect merely one among several different possibilities for organizing the overall computational functionality of the processing facility 104. The modules may, of course, be further partitioned, combined, or altered to distribute the functionality differently. The various modules may be implemented as hardware modules, software modules executed by a general-purpose processor, or a combination of both. For example, it is conceivable to implement the time-frequency transform module 112, which generally involves the same operations for each incoming ECG signal, with special-purpose circuitry to optimize performance, while implementing the index-builder module 114 and the analysis module 116 in software to provide flexibility for adjusting parameters and algorithms, e.g., in response to new medical data.

While the quantification of heart function in accordance herewith is, in general, not limited to any particular number of electrodes, the system 100 includes, in various embodiments, ten electrodes 102 to facilitate obtaining a standard twelve-lead ECG, as is routinely used in the medical arts. In accordance with the standard configuration, four of the ten electrodes (conventionally labeled LA, RA, LL, RL) are placed on the patient's left and right arms and legs; two electrodes (labeled V1 and V2) are placed between the fourth and fifth ribs on the left and right side of the sternum; a further, single electrode (labeled V3) is placed between V2 and V4 on the fourth intercostal space; one electrode (labeled V4) is placed between the fifth and sixth ribs at the mid-clavicular line (the imaginary reference line that extends down from the middle of the clavicle), and, in line therewith, another electrode (labeled V5) is positioned in the anterior axillary line (the imaginary reference line running southward from the point where the collarbone and arm meet), and the tenth electrode (labeled V6) is placed on the same horizontal line as these two, but oriented along the mid-axillary line (the imaginary reference point straight down from the patient's armpit). The electric potentials measured by electrodes V1 through V6 correspond to six of the twelve standard leads; the remaining six leads correspond to the following combinations of the signals measured with the individual electrodes: I=LA−RA; II=LL−RA; III=LL−LA; aVR=RA−½ (LA+LL); aVL=LA−½ (RA+LL); and aVF=LL−½ (RA+LA).

Figure 2:
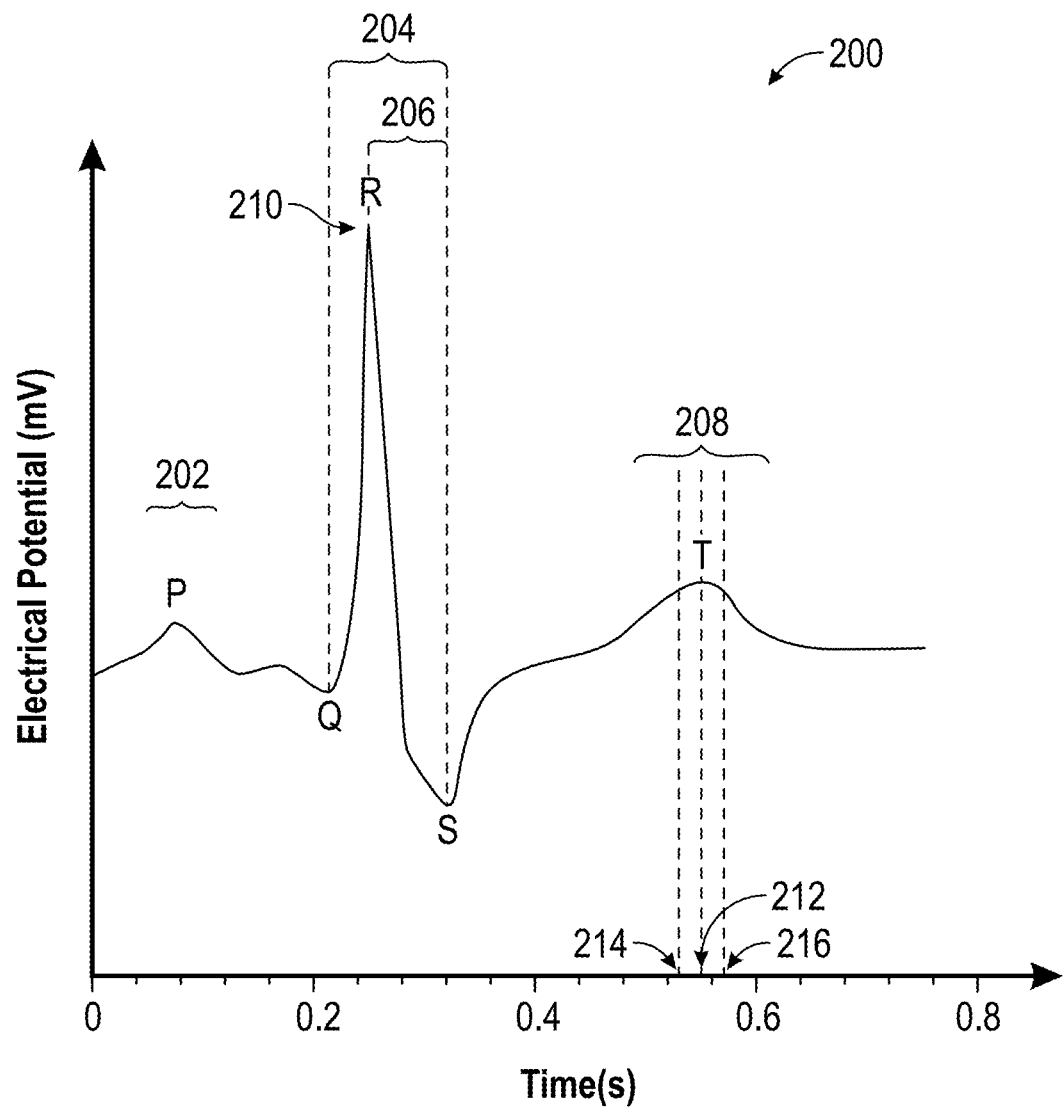
FIG. 2 is an example ECG, illustrating various segments and points in time used in accordance with various embodiments.

FIG. 2 schematically shows an example ECG 200 for a single cardiac cycle, illustrating the P wave 202, QRS complex 204 (which includes the RS segment 206), and T wave 208. As depicted, the electric potential usually reaches its maximum 210 at R during the QRS complex 204. However, the polarity of the signal may be inverted (such that the R peak has a negative value). Further, in some ECG signals, the S peak has a greater absolute value than the R peak. In fact, not every ECG unambiguously exhibits the features shown in the (rather typical) example ECG 200. This uncertainty can cause difficulty in attempts to normalize the signal based on a discrete feature of the ECG such as, e.g., the R peak. To circumvent this difficulty, various embodiments base normalization, instead, on a signal maximum and minimum identified across a time range, such as the time interval encompassing at least the RS segment 206 (and thus including both the R and the S peak if they are, in fact, clearly represented in the signal), irrespective of the feature to which that maximum or minimum corresponds (if any). FIG. 2 also illustrates certain points in time at which data is evaluated in accordance with various embodiments, such as the time 212 at which the T wave 208 assumes its maximum, and example early and late times 214, 216 bracketing the maximum of the T wave. In general, the early and late times 214, 216 may be anywhere on the rising edge and falling edge, respectively, of the T wave. In various embodiments, they are selected within ranges between the T wave maximum and points in time preceding and following the T wave maximum, respectively, at which the T wave assumes some specified fraction, e.g., half, of its maximum value.

In accordance herewith, the measured ECGs are transformed into two-dimensional time-frequency maps by a suitable mathematical transform, such as, for instance, wavelet transform. For a given continuous ECG signal x(t), the continuous wavelet transform is given by:

$$W(a, b) = \frac{1}{\sqrt{a}} \int_{-\infty}^{+\infty} \overline{\psi\left(\frac{t-b}{a}\right)} x(t)\, dt,$$

where $\psi$ is a selected wavelet, b corresponds to a shifted position in time and a to a scaling factor, and W(a,b) is the two-dimensional function of position in time and scale resulting from the transform, also called wavelet coefficients. Similarly, for a discretized ECG signal x(k) (where k is an integer), the continuous wavelet transform is given by:

$$W(a, b) = \frac{1}{\sqrt{a}} \sum_{k} x(k) \left( \int_{-\infty}^{(k+1)T} \overline{\psi\left(\frac{t-b}{a}\right)}\, dt - \int_{-\infty}^{kT} \overline{\psi\left(\frac{t-b}{a}\right)}\, dt \right),$$

where T is the sampling period. The wavelet selected for processing may be, for example, a Mexican hat wavelet, Morlet wavelet, Meyer wavelet, Shannon wavelet, Spline wavelet, or other wavelet known to those of ordinary skill in the art. Other well-known time-frequency transforms that may be used alternatively to continuous or discrete wavelet transform include, e.g., the short-term Fourier transform.

The time-frequency maps (such as, e.g., scalograms) generally include both positive and negative values. For an intuitive interpretation of the signal value of the time-frequency map as a measure of the electrical energy of the heart, however, the sign is not relevant (since, in a measure of the energy, the electrical potential is squared). Accordingly, in some embodiments, the absolute value of the signal value (or the square of the signal value) is taken at each time-frequency point, resulting in an unsigned time-frequency map. The unsigned time-frequency map may be advantageous, in particular, for display in a user interface (e.g., to a physician) since it avoids presenting information that is not of immediate, intuitively discernible clinical significance and is potentially distracting. On the other hand, since the signed time-frequency map contains generally more information than the unsigned time-frequency map, the computation of repolarization measures and indices may (but need not) be based on the signed map.

Figure 3A:
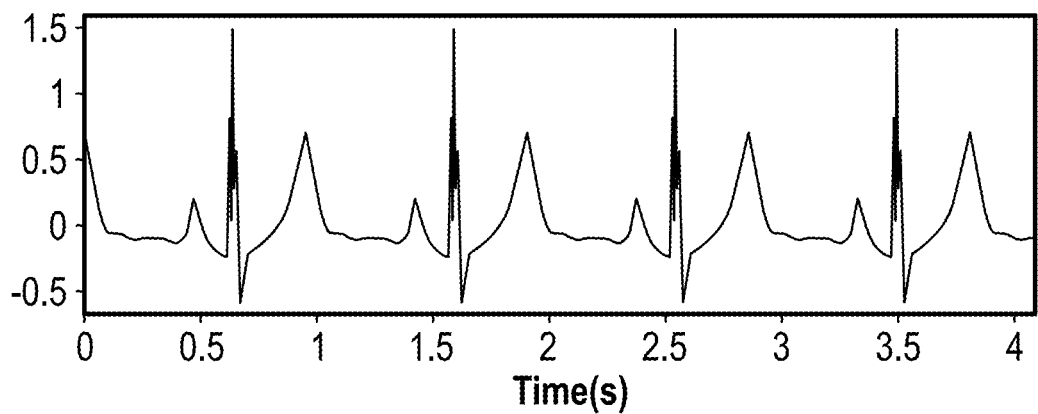
FIGS. 3A and 3B are graphs of an example ECG for a normal heart and a scalogram resulting from its wavelet transform, respectively, in accordance with one embodiment.
Figure 3B:
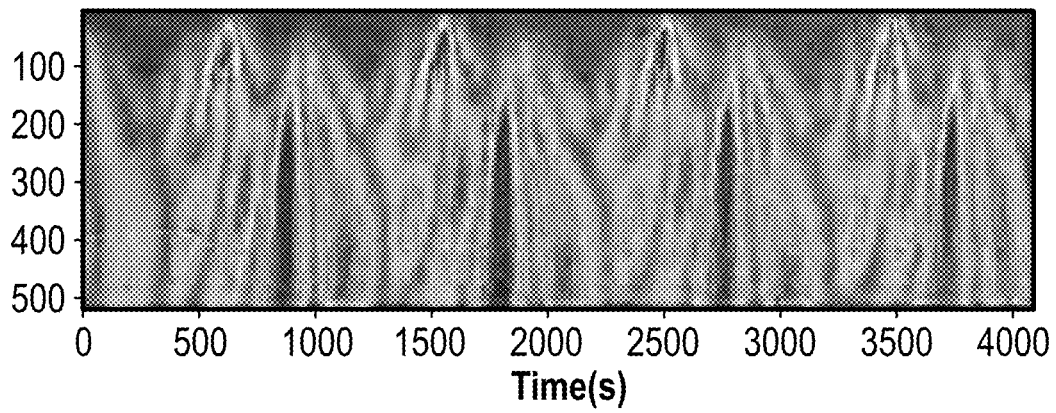
Figure 3C:
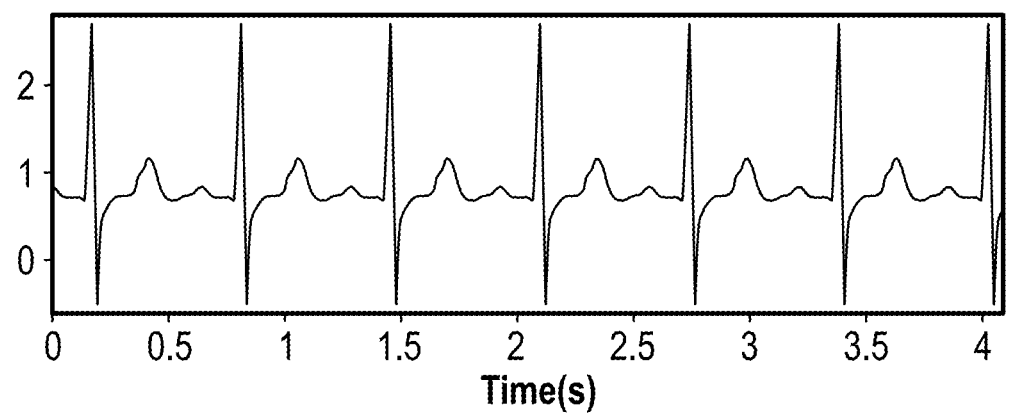
FIGS. 3C and 3D are graphs of an example ECG for an abnormal heart and a scalogram resulting from its wavelet transform, respectively, in accordance with one embodiment.
Figure 3D:
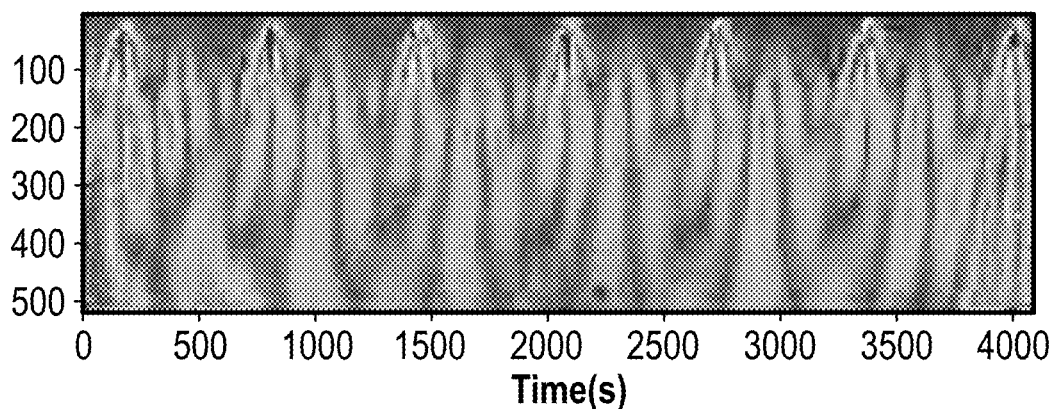

FIGS. 3A and 3B illustrate an example ECG for a normal heart and an unsigned scalogram resulting from its wavelet transform (followed by taking the absolute), respectively. In the scalogram, the position b corresponding to time is along the abscissa and the scale a (corresponding to frequency) along the ordinate, and the signal value W is encoded by color or intensity (e.g., gray-scale value). As can be seen, the various peaks of the normal ECG are reflected in relatively high intensity in the scalogram, allowing identification of the different ECG segments. For comparison, FIGS. 3C and 3D show an example ECG and associated scalogram, respectively, for an abnormal heart. Here, features that are prominent in the normal scalogram (e.g., the T wave) have rather low intensity. While this lower intensity generally tracks the lower values of the T wave in the ECG, it will be appreciated that the scalogram may provide better visual clues. Accordingly, the scalogram can aid a physician or other skilled clinician to assess heart functioning.

To facilitate meaningful comparisons between time-frequency maps derived from ECGs obtained simultaneously for different leads, the time-frequency maps may be normalized. Normalization may involve scaling and/or shifting signal values in the time-frequency map to map the range of signal values in the map (or at least a portion of the map, as explained below) to a specified numerical range (hereinafter "target range"), e.g., 0 to 255 or −128 to +127 (as are convenient ranges for binary representations, and can, in turn, be straightforwardly mapped onto color or gray-scale values for display). Using a particular normalization and the associated target range consistently not only across leads, but also across measurements taken at different times and/or even for different patients may also serve to improve comparability of data over time and across the patient population, as it eliminates or at least reduces overall signal-level variations, which are often not attributable to different heart conditions, allowing physicians to focus on the clinically relevant relative signal levels within a time-frequency map.

The normalization may be based on a regional maximum and minimum defined as the maximum and minimum of the time-frequency map across frequency and across time within a selected interval, and may then be applied to a second selected interval that may or may not be the same as the first selected interval. The maximum and minimum of the time-frequency map across frequency and across time within that second selected interval are hereinafter called the absolute maximum and minimum, and they may, but need not, coincide with the regional maximum and minimum. The first selected interval is typically, but not required to be, shorter than the second selected interval. In some embodiments, the regional maximum and minimum are determined across the entire time-frequency map, corresponding to the entire measurement time of the ECG from which it is derived, and the normalization is applied over that same range (such that the first and second selected intervals are equal). In other embodiments, the regional maximum and minimum are identified within a portion of the time-frequency map that is limited in its time dimension, e.g., to an integer number of heartbeats (e.g., disregarding partial heartbeats) or only a single heartbeat. A time-frequency map encompassing multiple heartbeats may, for instance, be broken up into portions corresponding to individual heartbeats, and each portion may be normalized separately (potentially resulting in some discontinuity of the signal values in the normalized time-frequency map); in this case, first and second selected intervals are likewise equal to each other. Normalization may even be based on a time interval encompassing only part of a heartbeat, selected to likely (but not certainly) include the absolute maximum and minimum. For instance, in some embodiments, regional maximum and minimum are determined within a portion of a time-frequency map that encompasses at least the RS segment. Note, however, that it is possible for, e.g., the T wave maximum to exceed the maximum in the QRS complex. In cases where the absolute maximum and minimum of the time-frequency map lie outside the portion of the map across which the regional maximum and minimum are determined, the normalization will result in signal values exceeding the target range. (Normalization may also be applied in the time domain. In this case, the regional minimum and maximum are across time over the selected time interval.)

Normalization may be applied according to the following equation:

$$n = (d - d_{min}) * \frac{(n_{max} - n_{min})}{(d_{max} - d_{min})} + n_{min},$$

where
  n is the normalized data point;
  $n_{min}$ is the normalized target-range minimum;
  $n_{max}$ is the normalized target-range maximum;
  d is the data point to be normalized;
  $d_{min}$ is the regional minimum; and
  $d_{max}$ is the regional maximum.

For example, to map onto the target range from 0 to 255, $n_{min}$ is 0 and $n_{max}$ is 255; in effect, this normalization shifts the time-frequency map to a minimum equal to zero and thereafter scales the shifted map based on its shifted regional maximum. More generally, the normalization shifts the time-frequency map to a minimum equal to $n_{min}$ and then scales the values of the shifted time-frequency map (taken relative to the minimum value) by the ratio of the difference between maximum and minimum of the target range to the difference between the regional maximum and minimum.

Normalization can be applied to signed as well as unsigned time-frequency maps. As will be appreciated, the result of the normalization will vary depending on whether the underlying time-frequency map is signed or unsigned. For example, when mapping a signed time-frequency map with a positive R peak and a negative S peak onto the target range from 0 to 255, several of the frequencies at the point in time corresponding to the S peak will map to or near zero. However, when the normalization is applied to the absolute value of the otherwise same time-frequency map, some frequencies at points in time between R and S will now map to or near zero whereas several of the frequencies at the point in time corresponding to the S peak will map onto a relatively larger positive number within the target range.

The time-frequency maps (optionally following normalization) may be displayed to a physician for evaluation. Alternatively or additionally, they may be further analyzed, in accordance with various embodiments, to determine various quantitative indicators of heart condition and function. To that end, various measures of the electric activity of the heart can be obtained, e.g., by determining extrema (i.e., maximum and/or minimum values) across frequency of the (normalized) time-frequency map (W or |W|) at certain points (or ranges) in time corresponding to distinctive features of the underlying ECGs, in particular, certain points (or ranges) in time associated with the T wave. Measures associated with the T wave are herein referred to as "repolarization measures" and include, for example, the maximum value at an early time within the T wave (REM), the maximum value at a late time within the T wave (RLM), or the maximum value at the peak of the T wave (RPM). Additional repolarization measures, e.g., including an integral over a time interval within the T wave, may also be defined and used to quantify heart condition.

From the repolarization measures determined in the time-frequency map, one or more repolarization indices may be derived, e.g., by averaging or based on information external to the ECG or time-frequency map. For example, if the repolarization measures are obtained based on ECGs covering multiple cardiac cycles, the individually determined maxima may be averaged over these cycles. Further, the various repolarization measures can generally be derived separately from different time-frequency maps obtained by transform of ECGs measured for different respective leads, and repolarization measures of the same type (e.g., the REMs) may be averaged across multiple leads. In particular, ventricular repolarization indices may be derived by averaging only across leads associated with the same (i.e., left or right) ventricle. For example, a ventricular index early measure for the right ventricle (VIEM_RV) may be calculated by (e.g., arithmetically) averaging over the REMs of leads V1 and V2, a ventricular index late measure for the right ventricle (VILM_RV) may be calculated by averaging over the RLMs of leads V1 and V2, and a ventricular index peak measure for the right ventricle (VIPM_RV) may be calculated by averaging over the RPMs of leads V1 and V2. Similarly, VIEM, VILM, and/or VIPM for the left ventricle (VIEM_LV, VILM_LV, and VIPM_RV) may be calculated by averaging over the REMs, RLMs, and RPMs, respectively, of leads V4, V5, and V6. In certain embodiments, further indices are derived from the preceding ones. For instance, a ventricular index average measure for the right ventricle (VIAM_RV) may be calculated as the sum of VIEM_RV and VILM_RV, divided by the heart rate (measured in beats per minute). Similarly, a ventricular index average measure for the left ventricle (VIAM_RV) may be calculated as the sum of VIEM_LV and VILM_LV, divided by the heart rate. Further, in some embodiments, an index for the heart as a whole is computed from respective indices for the left and right ventricles, e.g., by forming the ratio, difference, or some other function of left and right ventricular indices.

Further, while the repolarization measures are generally indicators of how well the heart functions, they can also be affected by age and gender, independently of any abnormal heart condition. To eliminate or at least reduce differences that do not result from heart abnormalities, the repolarization measures may be adjusted, when computing repolarization indices, with suitable age- and/or gender-dependent factors. In one embodiment, the adjustment distinguishes merely between male and female patients, using an adjustment factor of 1 for males (i.e., keeping the measures as is) and an adjustment factor smaller than one (e.g., 1/1.24) for females. In some embodiments, further refinements are made to distinguish between patients up to forty years old and patients older than forty years. For example, for females older than forty years, the adjustment factor may be decreased to 1/1.26. Other age-based classifications and adjustment factors may be implemented as well.

Figure 4:
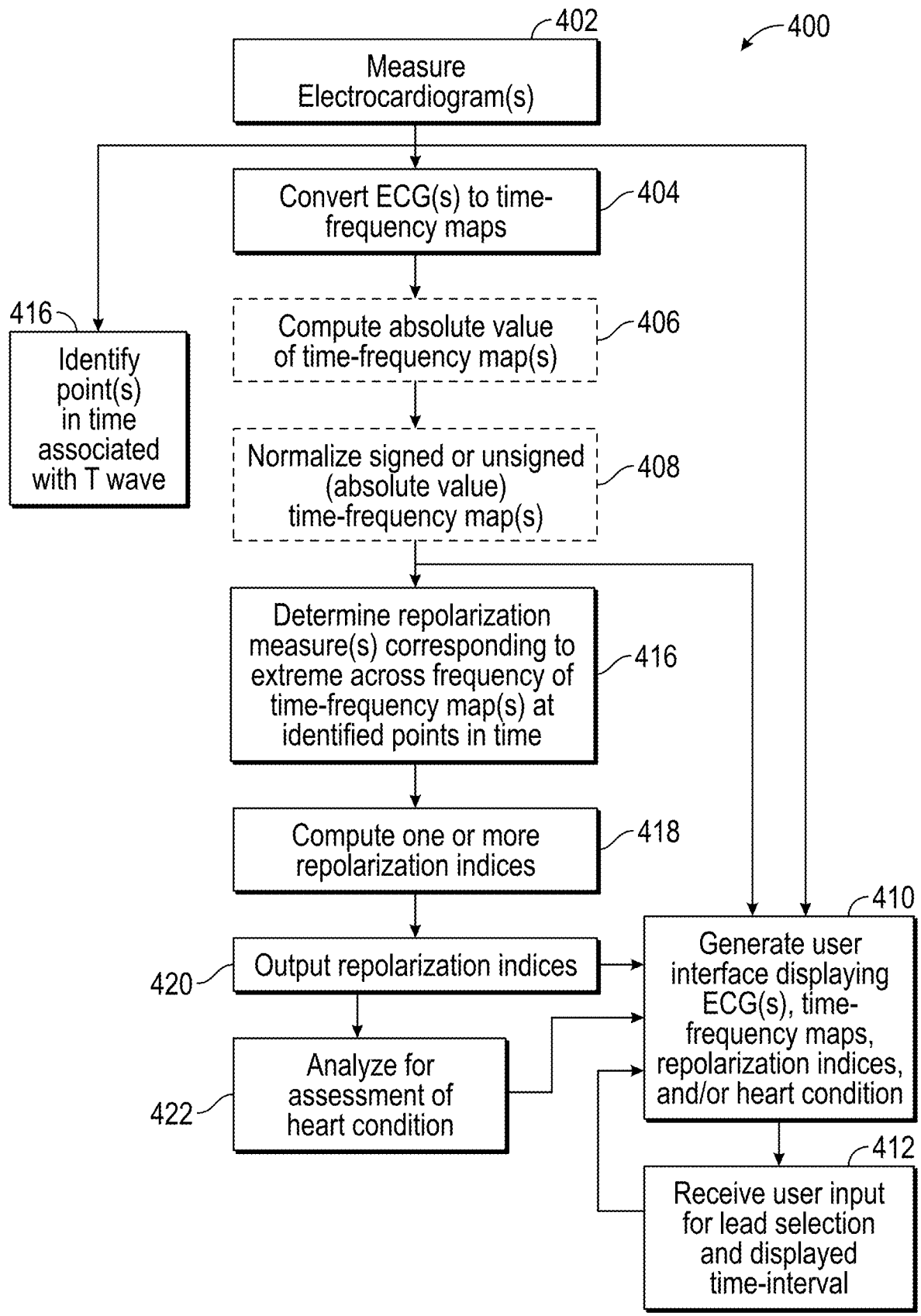
FIG. 4 is a flow chart of methods for quantifying and visualizing heart condition, in accordance with various embodiments.

FIG. 4 is a flow chart summarizing methods 400 for quantifying and visualizing heart condition in accordance with various embodiments. The method 400 involves measuring one or more ECGs associated with one or more respective leads (action 402), using one or more electrodes placed on a patient. In some embodiments, ten electrodes are used to obtain twelve leads. (The phrase "measuring electrocardiograms" is intended to encompass both the acquisition of electrocardiogram signals with the electrodes, and the digitization and/or initial processing of these signals to generate an electrocardiogram for each lead, which may include combining multiple electrocardiogram signals to obtain an electrocardiogram for a single lead, as described above.) In action 404, the ECG(s) are converted by time-frequency transform (e.g., wavelet transform) into one or more respective two-dimensional time-frequency maps (e.g., scalograms). The time-frequency map(s) may be used in the original signed form, or converted to unsigned map(s) by taking the absolute value at each time-frequency point (optional action 406), or both. Further, the time-frequency map(s) may be normalized (action 408), as described above. In some embodiments, for example, the time-frequency map is normalized based on the maximum and minimum identified in the time-frequency map across frequency and across a time interval encompassing at least the RS segment (and, in some embodiments, encompassing a full cardiac cycle (or heartbeat), multiple (an integer number of) cardiac cycles, or the entirety of the measurement time).

To visualize the heart condition, a user interface displaying the ECGs and/or corresponding time-frequency maps may be generated (action 410). The signal values in the time-frequency maps may be, e.g., color-coded or represented according to a gray scale. To focus the user's (e.g., an interpreting physician's) attention on the electrical energy of the heart, it may be beneficial, as indicated above, to present unsigned (i.e., absolute-value) time-frequency maps. Due to spatial constraints, the user interface may, at any given time, display only portions of the ECGs and time-frequency maps corresponding to time intervals smaller than the total measurement time. For example, out of data for a twelve-second interval, the display may be limited to a three-second subset. In addition, the number of ECGs and time frequency maps displayed at any given time may be limited, e.g., to three out of twelve ECGs and corresponding time-frequency maps. The displayed selection of ECGs and time-frequency map and the displayed time-range may depend on, and be adjusted based on, user input (received at 412). For example, a drop-down menu displayed next to each screen portion allocated to an ECG and time-frequency map may facilitate selection of any of the available leads. Further, the user may have the ability to scroll through the entire measurement time, e.g., with a conventional scrollbar, or with a swiping gesture performed, with a mouse-controlled cursor or on a touchscreen, in a region displaying an ECG or time-frequency map. In order to enable features within an ECG to be properly correlated with features in the corresponding time-frequency map, the displayed portions are temporally aligned (and, usually, temporally coextensive), and the alignment is retained (or, in other words, "locked in") as the user scrolls through the ECG or time-frequency map. Further, if ECGs and time-frequency maps are displayed for multiple leads, they may likewise be temporally aligned and temporally coextensive, and locked-in in their alignment as the user scrolls through any one of them.

To quantify heart condition, the time-frequency maps are analyzed in conjunction with the respective ECGs. Specifically, in action 414, one or more points in time associated with the T wave (e.g., early and late times and/or the time where the T wave peaks) are identified within an ECG. The corresponding time-frequency map is then analyzed at these points in time to determine, separately at each point in time (or within a small time interval surrounding the respective points in time), a maximum and/or minimum across frequency (action 416). The one or more extrema across frequency determined in the time-frequency maps at one or more points in time identified in respective ECGs constitute repolarization measures. Based on these repolarization measures, one or more repolarization indices can be determined in action 418. A repolarization index may be based on (and in the simplest case be equal to) a single repolarization measure or combine multiple repolarization measures (e.g., by averaging repolarization measures over leads or cardiac cycles). In addition, the repolarization index may include an adjustment factor that is based on the age or gender of the patient, or on some other characteristic of the patient or circumstance of the measurement. The computed repolarization indices may be output (in action 420) in various ways. For example, they may be included in the user interface (e.g., along with the ECGs and time-frequency maps) for display on-screen or in a printable report, communicated to the user in some other manner, or provided as input to another algorithm.

In some embodiments, the repolarization measures and/or repolarization indices are automatically analyzed (action 422), based on heuristics or empirical data, to obtain a qualitative assessment of heart condition. For example, based on an expectation that the early repolarization measure is greater than the late repolarization measure, observation of a late repolarization measure exceeding the early repolarization measure (for the same ECG and time-frequency map) may be taken as a sign of abnormal or impaired heart function, and communicated as such to the user. Similarly, since the left ventricular repolarization index should be greater than the right ventricular repolarization index for a healthy heart, the reverse relationship (i.e., a right ventricular repolarization index greater than the left repolarization index) indicates an abnormality or impairment that may be communicated to the user. Accordingly, comparisons between repolarization measures and repolarization indices may be used to assess heart function. Alternatively or additionally, repolarization measures and indices (properly normalized or computed from normalized time-frequency maps) may be compared against empirical thresholds. For example, with a normalization of the time-frequency maps to a range from 0 to 255, an early or late repolarization measure for the left or right ventricle that falls below a threshold in the range from 55-75 has been found to correlate strongly with some problem in heart function. In some embodiments, one or more repolarization indices are used to determine a myocardial energy category, e.g., distinguishing between high energy (corresponding to no or low functional impairment), moderate energy (corresponding to moderate functional impairment), and low energy (corresponding to high functional impairment). Comparisons of repolarization measures and/or repolarization indices against each other or against specified thresholds in various combinations may also serve to categorize heart function as normal, suspect, or abnormal.

Various modifications of the method 400 may be implemented. For example, as noted above, ventricular indices may be computed based on repolarization measures determined from values of the time-frequency map at one or more points in time other than early or late times, and/or over one or more ranges of time. Further, not every action of the depicted method 400 need be implemented in every embodiment. Accordingly, the depicted method 400 is to be understood as one example embodiment only.

Figure 5:
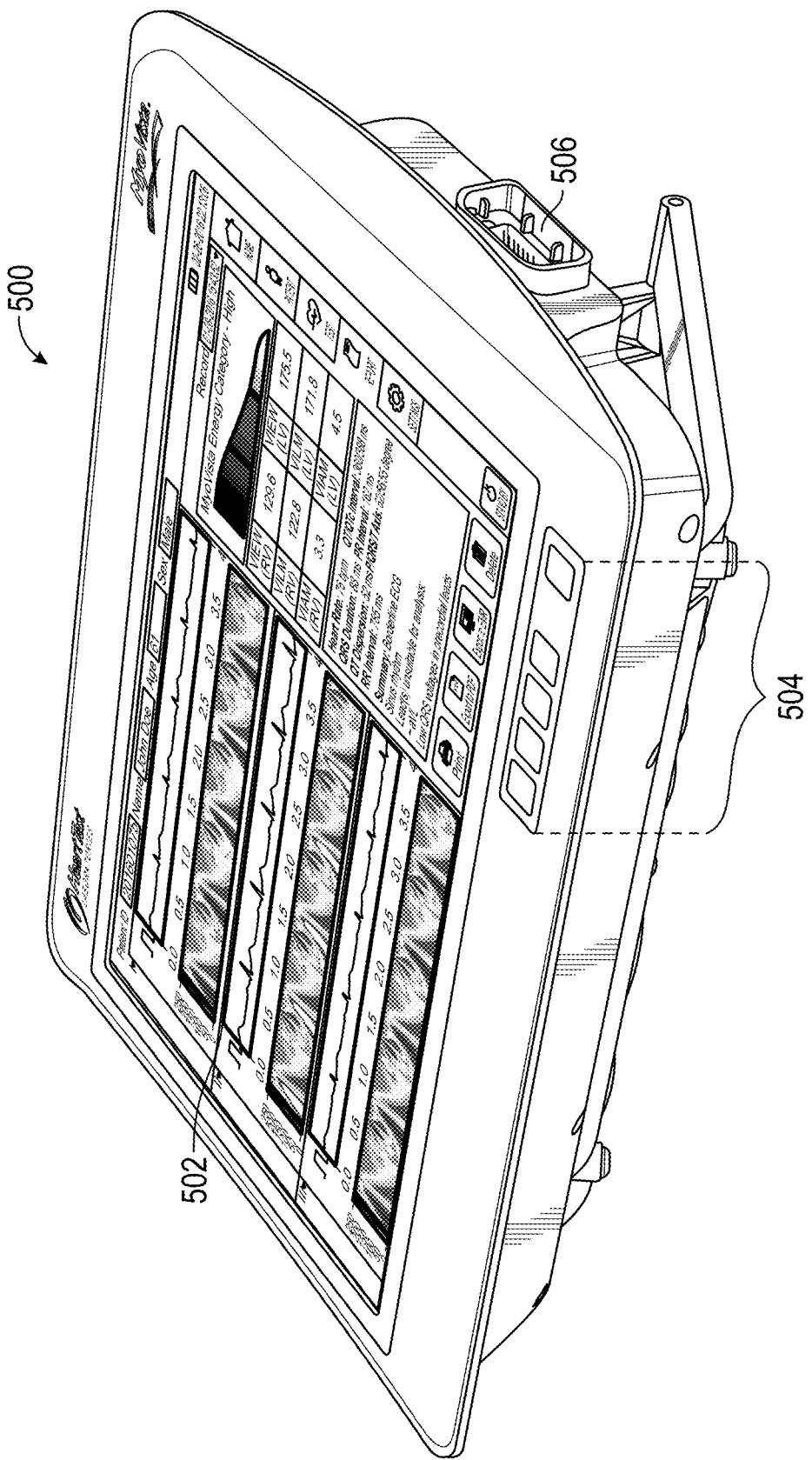
FIG. 5 is a perspective view of an example heart test device in accordance with various embodiments.

FIG. 5 shows an example heart test device 500 in perspective view. The depicted device takes the form of a tablet computer 500 including a touchscreen display 502 as well as a control panel 504 with physical buttons (e.g., to power the tablet 500 on/off). In some embodiments, as shown, the display 502 presents a multi-tab user interface, explained in more detail below with respect to FIGS. 6-10. Some of the tabs (shown along the right edge of the display 502) may be duplicated by the physical buttons of the control panel 504, allowing an operator to navigate between different screens and associated device functions in different ways. Electrodes for acquiring the ECG signals may be hooked up to the tablet computer 500 via a suitable connector 506 (e.g., a DB15 connector). The tablet 500 contains a general-purpose processor and volatile as well as non-volatile memory storing instructions for implementing the functional processing modules 110, 112, 114, 116, 118. Of course, in various alternative embodiments, the heart test device may take different form factors, such as that of a desktop computer, laptop computer, or smartphone (to name just a few), each with a suitable electrode interface, which may include custom circuitry for converting the electrode signals into digital signals suitable for further processing with software. Furthermore, an electrocardiography system providing the functionality described herein need not necessarily be implemented in a single device, but can be provided by multiple devices used in combination, e.g., a conventional ECG monitor connected to a general-purpose computer running software to implement the processing functionality described herein.

Figure 6:
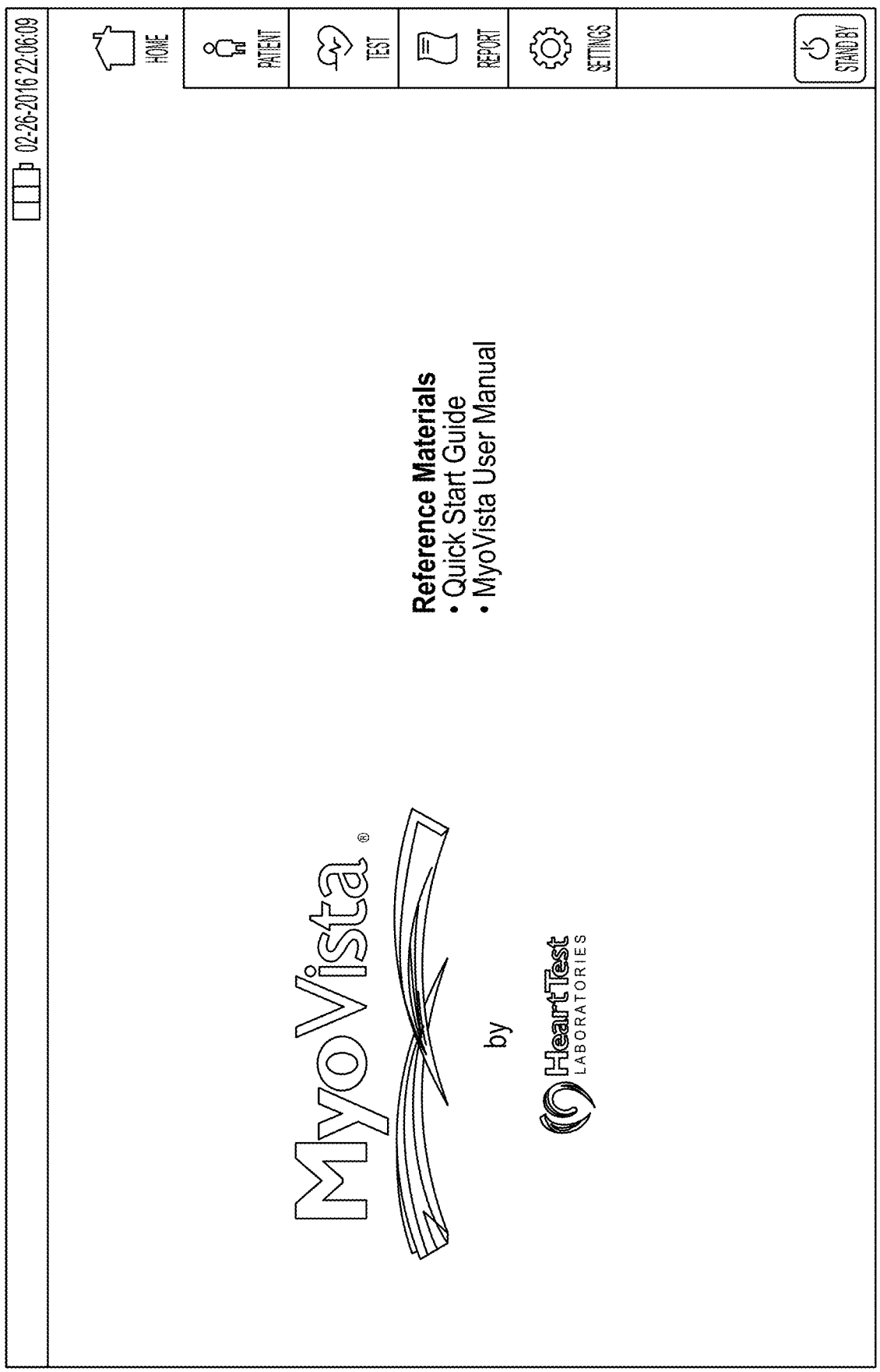
FIG. 6 is a user interface diagram for an example home screen in accordance with various embodiments.

Turing now to the user interface, FIG. 6 depicts an example home screen of the user interface as it may appear, e.g., when an operator first turns on the ECG test device 500. The home screen may, for example, provide links to reference materials such as a quick-start guide and a more comprehensive user manual. In accordance with one embodiment, as shown, the user interface includes multiple tabs, corresponding to multiple respective screens, that are visible in each screen (e.g., on the right hand side), allowing easy navigation between the screens. The tabs may be arranged in an order that corresponds to the natural workflow through the electrocardiography process, described further below. For example, in addition to the general tabs for the home screen and a settings screen, the tabs may include, in this order, a patient tab, a test tab, and a report tab.

Figure 7:
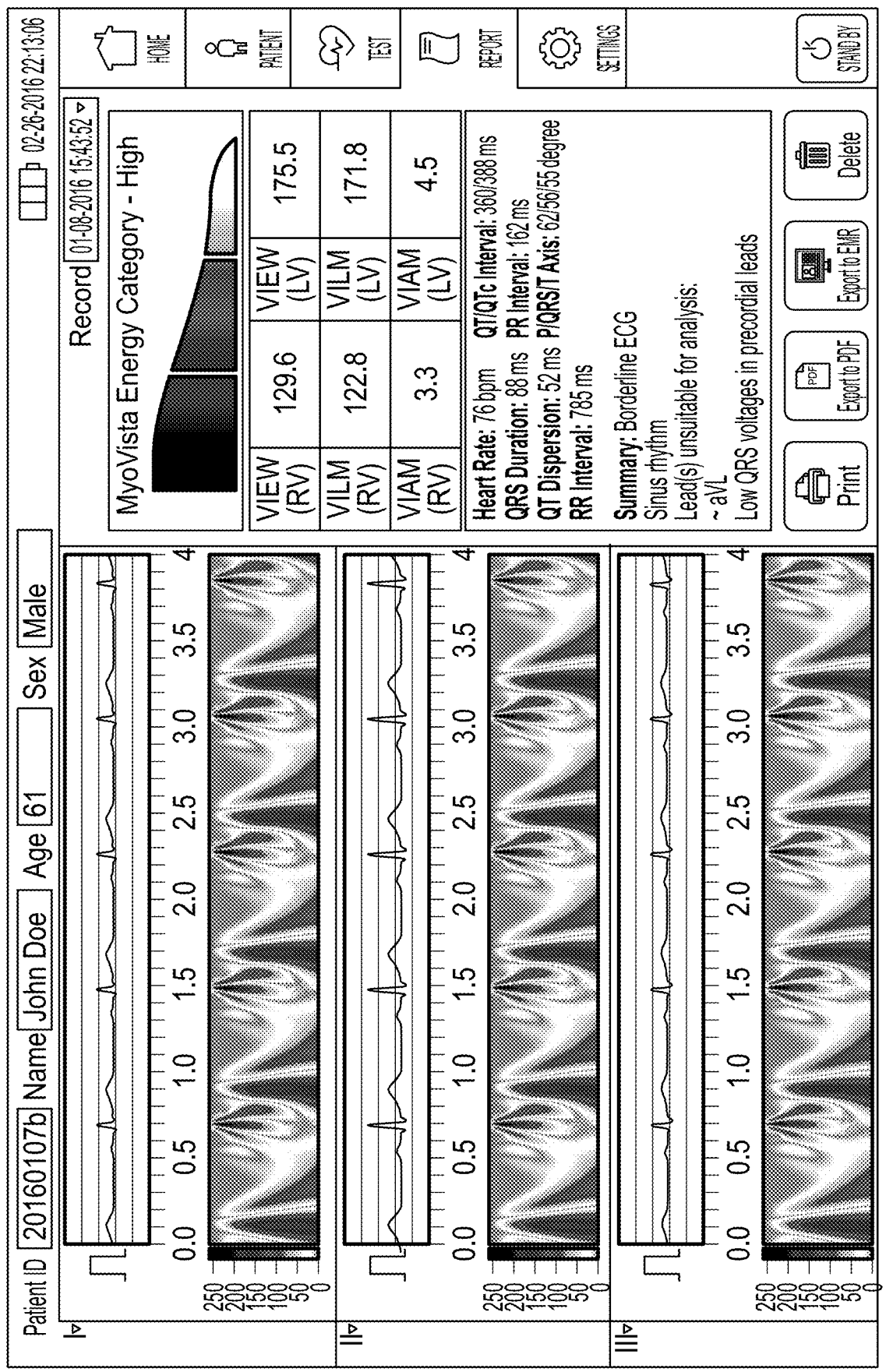
FIG. 7 is a user interface diagram showing an example report screen in accordance with various embodiments.

FIG. 7 illustrates an example report screen in accordance with various embodiments. As shown, the report screen may be partitioned into multiple screen portions arranged in an intuitive manner so as to allow the viewer to quickly locate the desired information. At the top of the screen, patient information, such as a unique patient identifier and the patient's name, as well as patient-specific parameters affecting the interpretation of the ECGs, such as age and gender, may be displayed, along with a record identifier composed of, e.g., a date and time stamp for the test. In a left panel, ECGs and time-frequency maps for one or more leads may be displayed, e.g., in a vertical arrangement. The time-frequency maps can visualize information not discernible from the ECGs from which they are derived, e.g., by providing a picture of the electrical energy of the heart during various stages within the cardiac cycle, and can be useful in detecting conditions such as myocardial ischemia, which are traditionally not diagnosed based on ECGs. ECGs are included in the display because of their familiarity to physicians and other medical practitioners and for the purpose of identifying temporally defined features of the signal, such as the QRS complex and T wave. In accordance with various embodiments, the signal value of the time-frequency map (e.g., the electrical potential or voltage that is plotted as a function of time and frequency) is encoded in a color scale (or, alternatively, as shown in the black-and-white drawings, in a grey scale). While the signal value itself, as resulting from the time-frequency (e.g., short-time Fourier or wavelet) transform applied to the ECG, may be a signed value (generally resulting in both positive and negative values across the map), the color-coded depicted value may be unsigned, as obtained from a signed value by computing the absolute value. Using unsigned signal values in the color-coded maps serves to represent the energy level of the time-dependent frequency content, independent of the phase of those frequencies, thus allowing the energy of either positive or negative phase to appear at the same point (along frequency) on the time-frequency map.

As described above, the ECGs and time-frequency maps may be analyzed, in accordance with various embodiments, to provide quantitative indices indicative of heart health and/or a qualitative assessment or categorization. The results of the analysis may be presented, as shown in the right panel of FIG. 7, in numerical, textual, and/or graphic form. For example, as shown, the right panel may include an "energy icon" representing the patient's overall heart health, a number of numerical indices (e.g., repolarization indices as described above) providing a more detailed picture underneath the icon, and a conventional Glasglow-analysis textual summary underneath the numerical indices. The Glasgow-analysis summary portion may display such metrics, derived from the ECGs, as the patient's heart rate and durations of certain ECG features (such as the QRS complex). In addition, it may summarize the quality and reliability of the test, e.g., based on signal-to-noise levels of various leads. Glasgow analysis is known to those of ordinary skill in the art, and will not be further elaborated upon herein.

Figure 8A:
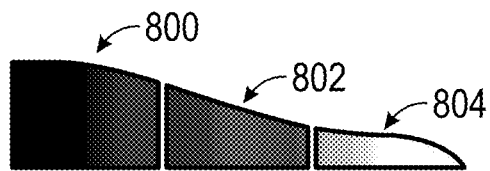
FIGS. 8A-8C show the energy icon contained in the report screen of FIG. 7 in three different states, corresponding to high myocardial energy, moderate myocardial energy, and low myocardial energy in accordance with various embodiments.
Figure 8B:
Figure 8C:

FIGS. 8A-8C show the energy icon of FIG. 7 in isolation in three different states, corresponding to high myocardial energy, moderate myocardial energy, and low myocardial energy, respectively. (These three states may be interpreted as normal, suspect, and abnormal conditions, respectively.) In the depicted embodiment, the energy icon is a segmented waveform symbol including three segments 800, 802, 804, which are filled, for a healthy patient (FIG. 8A), with a color gradient (shown, due to the conversion to black-and-white drawings, with variations in the grayscale value) mirroring the color scale of the time-frequency maps. For a patient with moderately impaired heart function or suspect heart condition (FIG. 7B), the first, left-most segment is greyed-out (shown by a uniform grey filling as distinguished from the previous variation). For a patient with strongly impaired or abnormal heart function (FIG. 6C), both the left segment and the middle segment are greyed out, symbolizing the much lower myocardial energy. The energy icon, thus, provides a clinician with an immediate visual clue as to the patient's heart health. As will be readily appreciated, the energy icon is amenable to finer gradation of the diagnostic assessment if modified to include more than three segments.

For a large number of leads, e.g., for a full twelve-lead ECG, it is generally impractical to display all twelve ECGs and associated time-frequency maps at once on the display. Accordingly, in various embodiments, the user is given the ability to scroll vertically through the ECG (left) panel to view different ones of the leads. For illustration, compare FIGS. 7 and 9, for example. While, in FIG. 7, ECGs and time-frequency maps for leads I, II, and III are shown, FIG. 9 illustrates the screen in a different scrolling position where, instead, ECGs and time-frequency maps for leads aVL and aVF can be seen.

Figure 10:
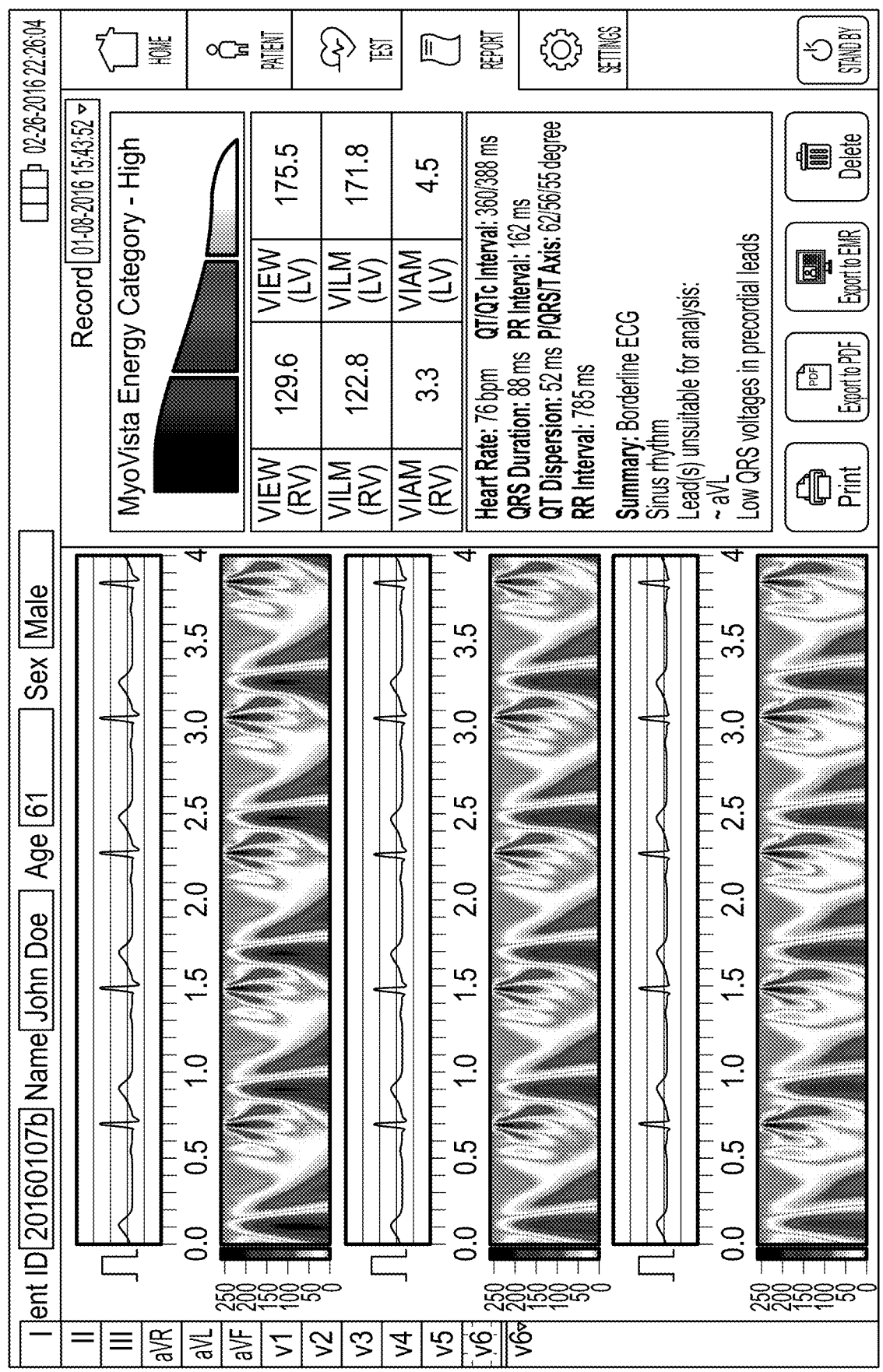
FIG. 10 is a user interface diagram showing an example report screen including a user-input control for lead selection in accordance with various embodiments.

Alternatively or additionally to being able to scroll through all leads, the user may be given the opportunity to select leads for display for each of the (sub-)portions of the left panel and thereby specify the order in which the leads are displayed. In various embodiments, the user-input controls for lead selection are drop-down menus displayed, initially in their closed state, adjacent the screen portions for respective ECGs and time-frequency maps. Each drop-down menu lists, once activated and opened by the operator, all twelve leads, facilitating user selection of any one of the leads for display within the current screen portion; FIG. 10 illustrates an opened drop-down menu for the first displayed lead. In some embodiments, once a new lead is selected, its position is swapped with the lead that previously occupied the respective screen portion. For example, if lead V1 is changed to lead V5 in the drop-down menu, the vertical positions of the respective ECGs and time-frequency maps will be swapped, and V1 will appear where V5 was previously located.

Figure 9:
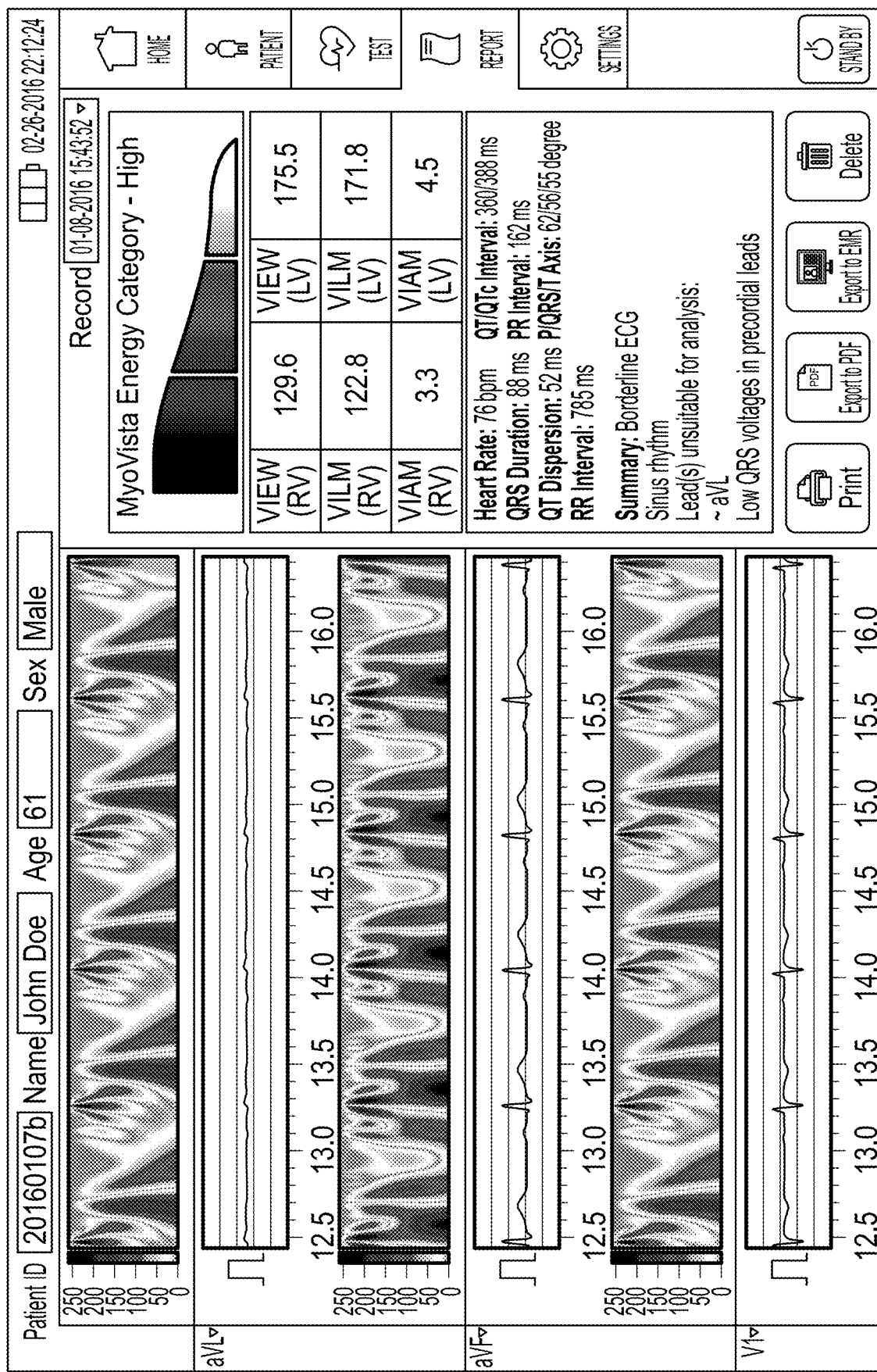
FIG. 9 is a user interface diagram showing a portion of the example report screen of FIG. 7 in a different scrolling position, in accordance with various embodiments.

As shown in the report screens depicted in FIGS. 7, 9, and 10, the ECGs may be displayed with the time axis extending horizontally (as is customary). In accordance with various embodiments, the corresponding time-frequency maps are likewise oriented with their time axes in the horizontal direction, and are temporally aligned with the ECGs, meaning that ECG and corresponding time-frequency map both show a given point in time at the same horizontal position. In addition to the temporal alignment within a screen portion showing an ECG and time-frequency map derived therefrom, the various screen portions displaying different ECGs (and corresponding time-frequency maps) may likewise be temporally aligned. Further, the left panel (and, indeed, the screen) may not be wide enough to display the ECGs and time-frequency maps in their entirety, covering the full acquisition period. Instead, the ECGs and time-frequency maps may be displayed partially, for a limited time range. The user interface may facilitate, however, a horizontal scroll by the operator through the ECG and/or time-frequency map to affect a temporal shift of the limited time range being displayed. During such a scroll, the ECG and corresponding time-frequency map may be "locked" so as to maintain their temporal alignment. Analogously, the other ECGs and time-frequency maps within the report screen may be locked to the screen portion being scrolled through, and thus move along with the scrolled through ECG/time-frequency map. A scroll can be effected in various ways, such as by a traditional scroll bar. In various embodiments, however, touchscreen capability of the display of the heart monitor device is exploited to allow scrolling via a swiping gesture performed on-screen in a direction substantially horizontal (and thus parallel to the time axis of the ECG), within a screen portion displaying the ECG and corresponding time-frequency map. From the swiping gesture, a shifted limited time range may be determined and applied to the shifting of the displayed ECG/time-frequency map portions. (As will be readily appreciated by one of ordinary skill in the art, the features of temporal alignment and temporal locking described above are not contingent upon the horizontal orientation of the time axis. Rather, it is conceivable that ECGs and/or corresponding time-frequency maps be displayed in a horizontal arrangement with their time axes pointing downward, in which case the temporal alignment would be vertical.)

Figure 11A:
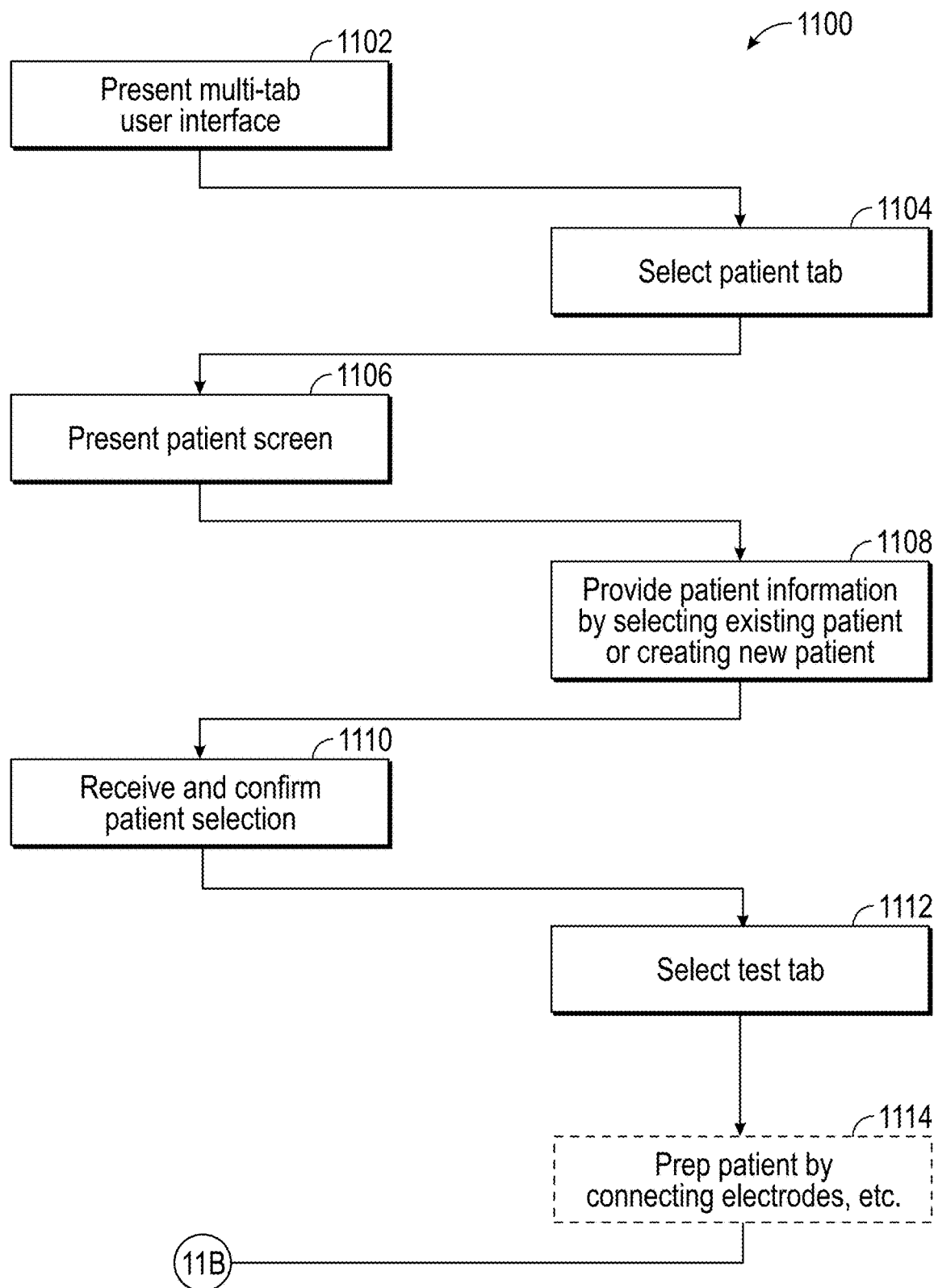
FIG. 11A-11B is a flow chart illustrating an electrocardiography workflow in accordance with various embodiments.
Figure 11B:
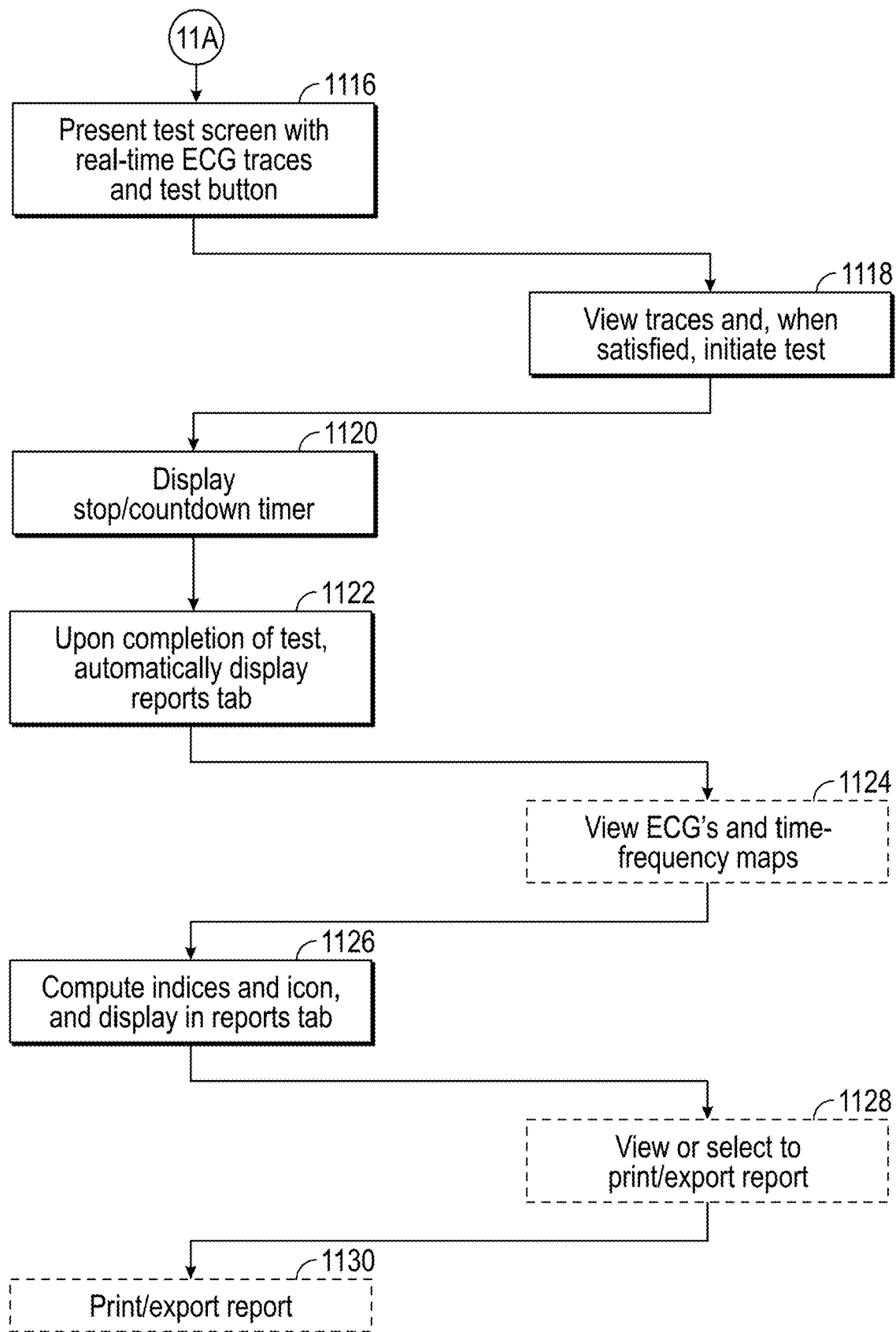

FIGS. 11A and 11B provide a flowchart illustrating an electrocardiography workflow 1100 supported by the depicted user interface, in accordance with various embodiments. The medical professional performing this workflow is, in a typical clinical setting (but not necessarily), a nurse (rather than a physician). Herein, the person operating the heart monitor device (e.g., to perform the workflow depicted in FIGS. 11A and 11B, or to subsequently view the results) is generically called the "operator." In FIGS. 11A and 11B, actions of the operator are shown on the right, and operations performed by the heart test device are depicted on the left. Referring to FIG. 11A, the operator, being presented with a multi-tab user interface (action 1102), generally starts by selecting the patient tab (action 1104). On the patient screen displayed as a result (action 1106), the operator can either select an existing patient from a list (optionally in conjunction with filtering based on operator-supplied search tokens), or create a new patient, e.g., by pressing a "New" button displayed on the screen and entering the relevant patient information (action 1108). Once a patient has been selected, a pop-up message may briefly appear on the patient screen to confirm the selection (action 1110).

The operator then navigates to the test screen (action 1112). If the patient has not already been prepped for the test (e.g., electrodes have been attached to patient, patient cable has been attached to heart monitor device and electrodes, etc.), the operator can do so at this stage (action 1114). Once available, the test screen displays real-time traces of the ECG signals (action 1116). The operator usually views the real-time ECG traces to assess whether all the electrodes are connected and the ECG signals are adequate to proceed with the test. Once the operator is satisfied with the quality of the real-time traces, he can initiate a test (action 1118) by pressing, e.g., a "Test" button provided on the test screen. Upon activation, this button may be replaced by a "Stop/Countdown Timer" button (action 1120) that displays the remaining test duration while the test is running, and also facilitates operator abortion of the test.

When the ECG test is complete, the user interface automatically navigates the operator to the reports screen (action 1122). The reports screen may initially (e.g., during the first 15-20 seconds), while the indices and energy icon are being computed, display merely the ECGs and corresponding time-frequency maps as well as a Glasgow analysis summary for viewing by the operator (action 1124). Optionally, a "Calculating . . . " or similar text message may alert the operator that additional information is forthcoming. An operator may simply wait for the computation of the icon and indices to complete. Once the reports screen is updated with the computed indices and icon (action 1126), the operator may view the results (action 1128). The operator may also be given the option to print or export the report (e.g., to an external USB drive) (action 1130). If the operator chooses to print the results (at 1128), a print-preview window may allow the operator to navigate the possibly multiple pages of the report as well as send the report to a network or physically attached printer. Printing is useful to allow a physician (who is not the operator) to view the test results offline before coming back into the exam room to discuss the results with the patient.

The embodiments describe hereinabove relate to the quantification and visualization of heart condition based on ECGs in conjunction with time-frequency maps derived therefrom. Some of the features described with reference to time-frequency maps may, however, also apply to, and be advantageous in the context of, the ECGs themselves. For example, for better comparability of the ECGs across leads, measurements, and patients, the ECGs may be normalized based on the absolute maximum and minimum of the ECG (in its entirety) or a portion thereof. Values of the normalized ECGs at certain points in time associated with the T wave may serve as repolarization measures for quantification of heart condition.

Certain embodiments are described herein as including a number of logic components or modules. Modules may constitute either software modules (e.g., code embodied on a non-transitory machine-readable medium or in a signal transmitted over a network) or hardware-implemented modules. A hardware-implemented module is a tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired) or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware-implemented modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice.

Figure 12:
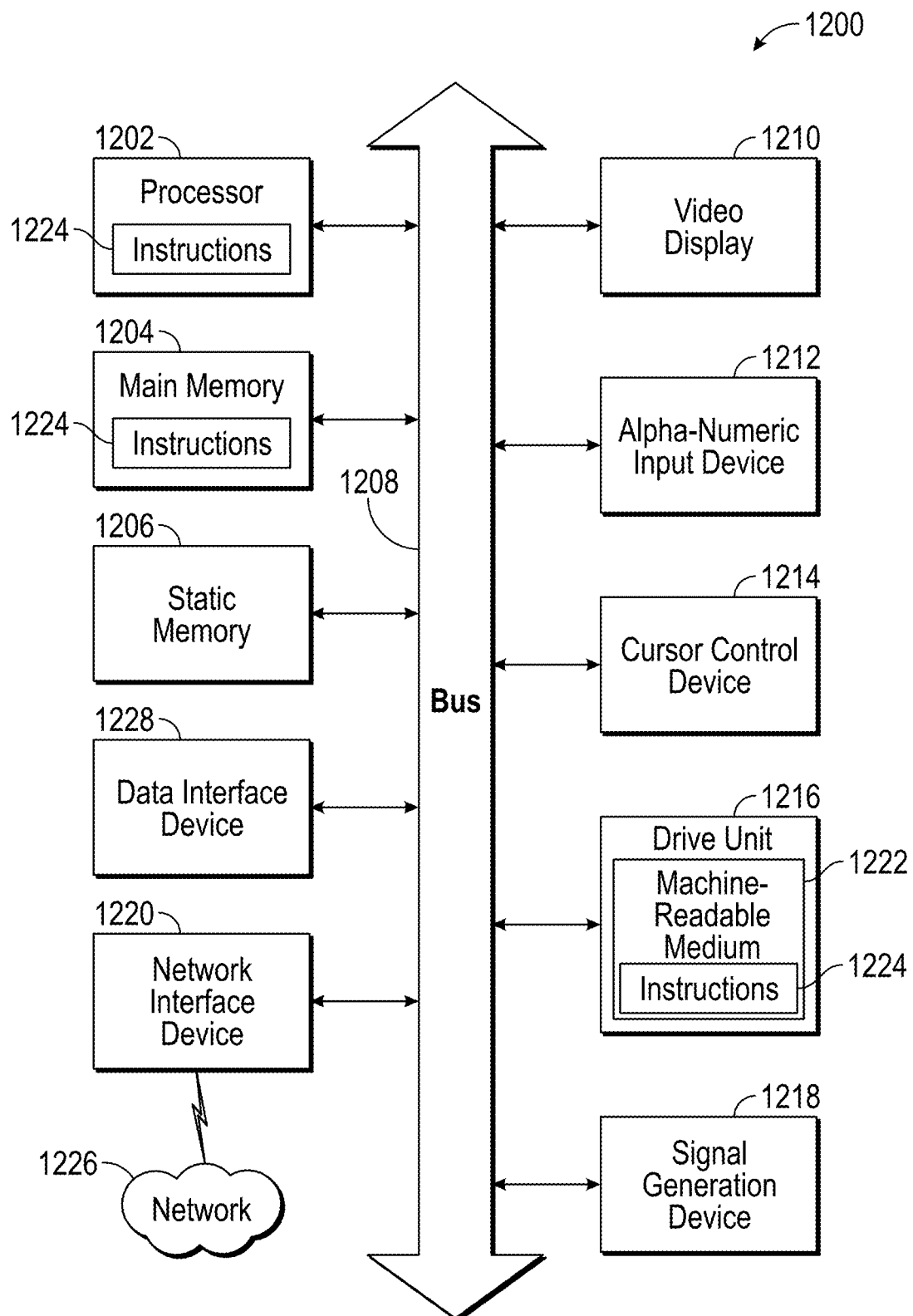
FIG. 12 is a block diagram of an example computer system as may serve as processing facility in accordance with various embodiments.

FIG. 12 is a block diagram of a machine in the example form of a computer system 1200 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. While only a single machine is illustrated, the term "machine" shall also be taken to include any collection of machines that individually or jointly execute a set (or multiple sets) of instructions to perform any one or more of the methodologies discussed herein. The example computer system 1200 includes one or more processors 1202 (e.g., a central processing unit (CPU), a graphics processing unit (GPU) or both), a main memory 1204 and a static memory 1206, which communicate with each other via a bus 1208. The computer system 1200 may further include a video display unit 1210 (e.g., a liquid crystal display (LCD) or a cathode ray tube (CRT)). The computer system 1200 also includes an alphanumeric input device 1212 (e.g., a keyboard), a user interface (UI) navigation device 1214 (e.g., a mouse), a disk drive unit 1216, a signal generation device 1218 (e.g., a speaker), a network interface device 1220, and a data interface device 1228 (such as, e.g., an electrode interface 106).

The disk drive unit 1216 includes a machine-readable medium 1222 storing one or more sets of instructions and data structures (e.g., software) 1224 embodying or utilized by any one or more of the methodologies or functions described herein. The instructions 1224 may also reside, completely or at least partially, within the main memory 1204 and/or within the processor 1202 during execution thereof by the computer system 1200, the main memory 1204 and the processor 1202 also constituting machine-readable media.

While the machine-readable medium 1222 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding, or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; CD-ROM and DVD-ROM disks, or other data-storage devices. Further, the term "machine-readable medium" shall be taken to include a non-tangible signal or transmission medium, including an electrical signal, a magnetic signal, an electromagnetic signal, an acoustic signal and an optical signal.

The following numbered examples are illustrative embodiments:

1. A method comprising: using one or more electrodes placed on a patient, measuring one or more electrocardiograms associated with one or more respective leads; converting the one or more electrocardiograms by time-frequency transform into one or more respective two-dimensional time-frequency maps; identifying, within the one or more electrocardiograms, one or more points in time associated with a T wave; determining, for at least one of the one or more time-frequency maps, one or more repolarization measures corresponding to extrema across frequency of the respective time-frequency map at the one or more points in time associated with the T wave; and outputting at least one repolarization index based on the one or more repolarization measures.

2. The method of example 1, further comprising normalizing each of the one or more time-frequency maps based at least in part on a difference between a maximum and a minimum identified in the respective time-frequency map across time in an interval encompassing an RS segment and across frequency, wherein the one or more repolarization measures are determined from the normalized time-frequency maps.

3. The method of example 2, wherein normalizing the one or more time-frequency maps comprises shifting each time-frequency map to a minimum equal to zero and thereafter scaling the respective time-frequency map based on the maximum.

4. The method of example 1 or example 2, wherein the time interval across which the maximum and minimum are identified in the time-frequency map encompasses at least one heartbeat.

5. The method of example 1 or example 2, wherein the time interval across which the maximum and minimum are identified in the time-frequency map encompasses a measurement time of the associated electrocardiogram in its entirety.

6. The method of example 1 or example 2, wherein the time interval across which the maximum and minimum are identified in the time-frequency map corresponds to an integer number of heartbeats.

7. The method of any one of examples 1-6, wherein the one or more points in time associated with the T wave fall within a time interval defined by points preceding and following a maximum of the T wave at which the T wave assumes half of its maximum value.

8. The method of example 7, wherein the one or more points in time associated with the T wave comprise a first point in time preceding the maximum of the T wave and a second point in time following the maximum of the T wave.

9. The method of example 8, wherein a first repolarization measure corresponding to an extremum at the first point in time and a second repolarization measure corresponding to an extremum at the second point in time are determined, the method further comprising comparing the first and second repolarization measures.

10. The method of example 9, further comprising determining a heart condition based on the comparison.

11. The method of example 10, further comprising communicating the heart condition to a user.

12. The method of example 10 or example 11, wherein an abnormal heart condition is determined based on the second repolarization measure being greater than the first repolarization measure.

13. The method of any one of examples 1-12, wherein electrocardiograms are measured and respective repolarization measures are determined for at least one lead associated with a left ventricle of the patient's heart and at least one lead associated with a right ventricle of the patient's heart, and wherein a left ventricular repolarization index based on the at least one repolarization measure determined for the left ventricle is compared with a right ventricular repolarization index based on the at least one repolarization measure determined for the right ventricle.

14. The method of example 13, further comprising determining a heart condition based on the comparison.

15. The method of example 14, further comprising communicating the heart condition to a user.

16. The method of example 14 or example 15, wherein an abnormal heart condition is determined based on the right ventricular repolarization index being greater than the left ventricular repolarization index.

17. The method of any one of examples 13-16, wherein the left ventricular repolarization index comprises an average over multiple repolarization measures, corresponding to extrema at a selected one of the points in time, determined based on electrocardiograms measured for multiple respective leads associated with the left ventricle, and the right ventricular repolarization index is determined by averaging over multiple repolarization measures, corresponding to extrema at the selected point in time, determined based on electrocardiograms measured for multiple respective leads associated with the right ventricle.

18. The method of any one of examples 1-17, wherein the at least one repolarization index comprises an average over two or more repolarization measures.

19. The method of example 18, wherein the average is taken over two or more heart beats.

20. The method of example 18 or example 19, wherein the average is taken over two or more leads.

21. The method of any one of examples 1-20, wherein the at least one repolarization index comprises an adjustment factor that is based on at least one of an age or a gender of the patient.

22. The method of any one of examples 1-21, wherein the at least one repolarization index is computed from the at least one repolarization measure and a heart rate of the patient.

23. The method of any one of examples 1-22, wherein the time-frequency transform comprises a wavelet transform and the time-frequency map comprises a scalogram.

24. The method of example 23, wherein the time-frequency transform comprises a continuous wavelet transform.

25. The method of any one of examples 1-24, wherein the time-frequency maps are absolute-value maps.

26. The method of any one of examples 1-25, further comprising determining a heart condition based on a comparison of the at least one repolarization index against a threshold.

27. The method of example 26, further comprising communicating the heart condition to a user.

28. The method of example 26 or example 27, wherein an abnormal heart condition is determined based on the at least one repolarization index being below the threshold.

29. The method of any one of examples 1-28, wherein the outputting comprises displaying the at least one repolarization index in a user interface.

30. A heart test system comprising: an electrode interface configured to receive one or more electrocardiogram signals via one or more respective electrodes connectable to the electrode interface; and a processing facility communicatively coupled to the electrode interface and configured to: generate, from the one or more electrocardiogram signals, one or more electrocardiograms for one or more respective leads; convert the one or more electrocardiograms by time-frequency transform into one or more respective two-dimensional time-frequency maps; identify, within the one or more electrocardiograms, one or more points in time associated with a T wave; determine, for at least one of the one or more time-frequency maps, one or more repolarization measures corresponding to extrema of the respective time-frequency map at the one or more points in time associated with the T wave; and output at least one repolarization index based on the one or more repolarization measures.

31. The system of example 30, wherein the electrode interface and the processing facility are integrated into a single heart test device.

32. The system of example 30 or example 31, wherein the processing facility is configured to implement the method of any one of examples 2-29.

33. One or more computer-readable media storing instructions for processing one or more electrocardiograms associated with one or more respective leads, the instructions, when executed by one or more computer processors, causing the one or more computer processors to: convert the one or more electrocardiograms by time-frequency transform into one or more respective two-dimensional time-frequency maps; identify, within the one or more electrocardiograms, one or more points in time associated with a T wave; determine, for at least one of the one or more time-frequency maps, one or more repolarization measures corresponding to extrema of the respective time-frequency map at the one or more points in time associated with the T wave; and output at least one repolarization index based on the one or more repolarization measures.

34. The one or more computer-readable media of example 33, storing instructions which, when executed by the one or more computer processors, cause the one or more computer processors to carry out the method of any one of examples 2-29.

35. A method comprising: using one or more electrodes placed on a patient, measuring one or more electrocardiograms associated with one or more respective leads; converting the one or more electrocardiograms by time-frequency transform into one or more corresponding two-dimensional time-frequency maps; and generating a user interface displaying, for at least one of the one or more electrocardiograms, at least a portion of the electrocardiogram and, in temporal alignment therewith, a temporally coextensive portion of the corresponding time-frequency map.

36. The method of example 35, further comprising: identifying, within the one or more electrocardiograms, one or more points in time associated with a T wave; determining at least one repolarization index from values of the one or more time-frequency maps at the one or more points in time associated with the T wave; and causing the at least one repolarization index to be displayed in the user interface.

37. The method of example 36, wherein, for multiple leads, multiple respective electrocardiograms are measured and transformed into multiple corresponding time-frequency maps, and wherein the generated user interface displays only a subset comprising fewer than all of the multiple electrocardiograms and corresponding time-frequency maps, the at least one repolarization index being independent from a selection of electrocardiograms and time-frequency maps for inclusion in the displayed subset.

38. The method of example 36 or 37, wherein generating the user interface comprises representing unsigned values of the one or more time-frequency maps based on a color scale, and wherein the at least one repolarization index is determined from signed values of the one or more time-frequency maps at the one or more points in time associated with the T wave.

39. The method of any one of examples 36-38, further comprising determining a heart condition based on the at least one repolarization index and generating, for display within the user interface, an icon indicative of the heart condition.

40. The method of example 39, wherein the icon comprises a segmented waveform symbol signifying, via a number of greyed-out segments within the otherwise colored waveform symbol, a degree of impairment of heart function.

41. The method of any one of examples 35-40, wherein the displayed portions of the electrocardiogram and the corresponding time-frequency map encompass less than an entire measurement time of the electrocardiogram, the method further comprising temporally shifting, responsive to user input, the displayed portions of the electrocardiogram and the corresponding time-frequency map.

42. The method of example 41, wherein the displayed portions are temporally shifted based on user input comprising a scrolling action associated with at least one of a screen portion displaying the electrocardiogram or a screen portion displaying the corresponding time-frequency map.

43. The method of example 42, wherein the scrolling action comprises a swiping gesture performed within a screen portion displaying the electrocardiogram or the corresponding time-frequency map and in a direction substantially parallel to a time axis of the electrocardiogram and the corresponding time-frequency map.

44. The method of example 43, wherein the scrolling action is performed on a touchscreen.

45. The method of any one of examples 35-44, wherein the generated user interface displays at least portions of multiple electrocardiograms and corresponding time-frequency maps for multiple respective leads, the portions of the electrocardiograms and time-frequency maps for different ones of the leads being temporally coextensive and temporally aligned with each other.

46. The method of example 45, further comprising temporally shifting, responsive to a scrolling action associated with one of the electrocardiograms or the corresponding time-frequency map, the displayed portions of all of the multiple electrocardiograms and corresponding time-frequency maps.

47. The method of any one of examples 35-46, wherein, for multiple leads, multiple respective electrocardiograms are measured and transformed into multiple corresponding time-frequency maps, and wherein the generated user interface displays only a subset comprising fewer than all of the multiple electrocardiograms and corresponding time-frequency maps, the subset being selectable via one or more user-input control elements included in the user interface.

48. The method of example 47, wherein the user interface comprises multiple screen portions, each facilitating, via an associated one of the user-input control elements, user selection of one of the measured electrocardiograms and the corresponding time-frequency map for display in the screen portion.

49. The method of example 48, wherein each of the user-input control elements comprises a drop-down menu displaying, upon activation, user-selectable symbols for all of the leads.

50. A heart test system comprising: an electrode interface configured to receive one or more electrocardiogram signals via one or more respective electrodes connectable to the electrode interface; a display device; and a processing facility configured to generate a user interface screen based at least in part on the received one or more electrocardiogram signals and to cause display of the user interface screen on the display device, wherein generating and causing display of the user interface screen comprises: generating, from the one or more electrocardiogram signals, one or more electrocardiograms for one or more respective leads; converting the one or more electrocardiograms by time-frequency transform into one or more corresponding two-dimensional time-frequency maps; generating a user interface displaying, for at least one of the one or more electrocardiograms, at least a portion of the electrocardiogram and, in temporal alignment therewith, a temporally coextensive portion of the corresponding time-frequency map.

51. The system of example 50, wherein the electrode interface, the display device, and the processing facility are integrated into a single heart test device.

52. The system of example 50 or example 51, wherein the display device comprises a touchscreen.

53. The system of any one of examples 50-52, wherein the processing facility is configured to implement the method of any one of examples 36-49.

54. One or more computer-readable media storing instructions for processing one or more electrocardiograms associated with one or more respective leads, the instructions, when executed by one or more computer processors, causing the one or more processors to: convert the one or more electrocardiograms by time-frequency transform into one or more corresponding two-dimensional time-frequency maps; and generate a user interface displaying, for at least one of the one or more electrocardiograms, at least a portion of the electrocardiogram and, in temporal alignment therewith, a temporally coextensive portion of the corresponding time-frequency map.

55. The one or more computer-readable media of example 54, storing instructions which, when executed by the one or more computer processors, cause the one or more processors to carry out the method of any one of examples 35-49.

56. A heart test device comprising: an electrode interface configured to receive a plurality of electrocardiogram signals via a plurality of respective electrodes connectable to the electrode interface; a display device; and a processing facility comprising circuitry configured to generate a user interface screen based at least in part on the received electrocardiogram signals and to cause display of the user interface screen on the display device, wherein generating and causing display of the user interface screen comprises: generating for display, based on the electrocardiogram signals, a plurality of one-dimensional time-dependent electrocardiograms for a plurality of respective leads; causing at least partial display of a subset of the electrocardiograms, corresponding to a subset of the leads, in multiple respective screen portions of the user interface screen; causing display, within each of the screen portions adjacent the electrocardiogram at least partially displayed therein, of a user-input control element facilitating user selection of any one of the plurality of leads; and in response to user selection of one of the leads via the user-input control elements, causing at least partial display, within the corresponding screen portion, of the electrocardiogram for the selected lead.

57. The device of example 56, wherein the user-input control element comprises a drop-down menu displaying, upon activation, user-selectable symbols for all of the leads.

58. The device of example 56 or example 57, wherein the at least partially displayed electrocardiograms are temporally aligned.

59. The device of any of examples 56-58, wherein generating and causing display of the user interface screen further comprises: generating for display, from each of the one-dimensional time-dependent electrocardiograms for the plurality of leads, a corresponding two-dimensional time-frequency map; causing at least partial display of a subset of the two-dimensional time-frequency maps, corresponding to the subset of the leads, each time-frequency map of the subset being displayed along with the corresponding electrocardiograms within the corresponding screen portion; and, in response to user selection of one of the leads via the user-input control elements, causing at least partial display of the time-frequency map for the selected lead in the corresponding screen portion along with the corresponding electrocardiogram.

60. A method comprising: measuring a plurality of electrocardiogram signals using a plurality of respective electrodes placed on a patient; using a processing facility to generate a user interface screen based at least in part on the received electrocardiogram signals and to cause display of the user interface screen on a display device, wherein generating and causing display of the user interface screen comprises: generating for display, based on the electrocardiogram signals, a plurality of one-dimensional time-dependent electrocardiograms for a plurality of respective leads; causing at least partial display of a subset of the electrocardiograms, corresponding to a subset of the leads, in multiple respective screen portions of the user interface screen; causing display, within each of the screen portions adjacent the electrocardiogram displayed therein, of a user-input control element facilitating user selection of any one of the plurality of leads; and in response to user selection of one of the leads via the user-input control elements, causing at least partial display, within the corresponding screen portion, of the electrocardiogram for the selected lead.

61. A heart test device comprising: an electrode interface configured to receive one or more electrocardiogram signals via one or more respective electrodes connectable to the electrode interface; a display device; and a processing facility comprising circuitry configured to generate a user interface screen based at least in part on the received one or more electrocardiogram signals and to cause display of the user interface screen on the display device, wherein generating and causing display of the user interface screen comprises: generating, from the one or more electrocardiogram signals, for each of one or more leads, a one-dimensional time-dependent electrocardiogram; using a time-frequency transform to compute, from each of the one or more electrocardiograms, a corresponding two-dimensional time-frequency map representing an unsigned signal value as a function of time and frequency; causing, for at least one of the leads, display of temporally aligned portions of the electrocardiogram and the corresponding time-frequency map, the unsigned signal value of the time-frequency map being color-coded.

62. A method comprising: presenting, on a display of an electronic heart monitor device, a multi-tab user interface configured to guide an operator of the device through a electrocardiography workflow, the multi-tab user interface comprising at least a patient tab, a test tab, and a report tab; in response to operator selection of the patient tab, presenting a patient screen comprising one or more first user-input control elements facilitating operator selection of a patient among a list of existing patients and one or more second user-input control elements facilitating operator entry of patient information for a new patient; in response to operator selection of the test tab and following connection of one or more electrodes to the heart monitor device, presenting a test screen comprising one or more real-time traces of one or more respective electrocardiogram signals measured by the one or more connected electrodes and further presenting a third user-input control element facilitating operator initiation of an electrocardiogram test; upon operator selection of the third user-input control element, causing acquisition of one or more electrocardiogram signals throughout a specified test duration and presenting, within the test screen, a fourth user-input control element displaying a countdown timer based on the specified test duration and facilitating operator abortion of the electrocardiogram test; upon completion of the electrocardiogram test, automatically presenting a reports screen associated with the reports tab, the reports comprising report information including at least one electrocardiogram computed based on the one or more electrocardiogram signals and one or more fifth user-input control elements facilitating operator initiation of at least one of printing or exporting the report information.

Although the invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

The invention claimed is:

1. A method comprising:
  receiving one or more electrocardiograms acquired for a patient for one or more respective leads;
  converting the one or more electrocardiograms by time-frequency transform into one or more respective two-dimensional time-frequency maps;
  identifying, within the one or more electrocardiograms, one or more points in time associated with a T wave;
  determining, for at least one of the one or more time-frequency maps, one or more repolarization measures corresponding to extrema of the respective time-frequency map at the one or more points in time associated with the T wave; and
  outputting at least one repolarization index based on the one or more repolarization measures.

2. The method of claim 1, further comprising normalizing each of the one or more time-frequency maps based at least in part on a difference between a maximum and a minimum identified in the respective time-frequency map across time in an interval encompassing an RS segment and across frequency, wherein the one or more repolarization measures are determined from the normalized time-frequency maps.

3. The method of claim 1, wherein the one or more points in time associated with the T wave comprise a first point in time preceding the maximum of the T wave and a second point in time following the maximum of the T wave.

4. The method of claim 3, further comprising comparing a first repolarization measure corresponding to an extremum at the first point in time with a second repolarization measure corresponding to an extremum at the second point in time.

5. The method of claim 4, further comprising determining a heart condition based on the comparison.

6. The method of claim 5, wherein an abnormal heart condition is determined based on the second repolarization measure being greater than the first repolarization measure.

7. The method of claim 1, wherein the electrocardiograms and respective repolarization measures include electrocardiograms and repolarization measures for at least one lead associated with a left ventricle of the patient's heart and at least one lead associated with a right ventricle of the patient's heart, the method further comprising comparing a left ventricular repolarization index determined based on the at least one repolarization measure determined for the left ventricle with a right ventricular repolarization index determined based on the at least one repolarization measure determined for the right ventricle.

8. The method of claim 7, further comprising determining an abnormal heart condition based on the right ventricular repolarization index being greater than the left ventricular repolarization index.

9. The method of claim 1, wherein the time-frequency transform comprises a continuous wavelet transform and the time-frequency map comprises a scalogram.

10. The method of claim 1, further comprising determining a heart condition based on a comparison of the at least one repolarization index against a threshold.

11. A heart test system comprising:
one or more computer processors; and
memory storing instructions for execution by the one or more computer processors, the instructions, when executed, causing the one or more computer processors to process one or more electrocardiograms acquired for a patient for one or more respective leads by performing operations comprising:
converting the one or more electrocardiograms by time-frequency transform into one or more respective two-dimensional time-frequency maps;
identifying, within the one or more electrocardiograms, one or more points in time associated with a T wave;
determining, for at least one of the one or more time-frequency maps, one or more repolarization measures corresponding to extrema of the respective time-frequency map at the one or more points in time associated with the T wave; and
causing display to a user, on a display device or in a printable report, of at least one repolarization index determined based on the one or more repolarization measures.

12. The system of claim 11, the operations further comprising:
normalizing each of the one or more time-frequency maps based at least in part on a difference between a maximum and a minimum identified in the respective time-frequency map across time in an interval encompassing an RS segment and across frequency, wherein the one or more repolarization measures are determined from the normalized time-frequency maps.

13. The system of claim 11, wherein the one or more points in time associated with the T wave comprise a first point in time preceding the maximum of the T wave and a second point in time following the maximum of the T wave.

14. The system of claim 13, the operations further comprising:
comparing a first repolarization measure corresponding to an extremum at the first point in time with a second repolarization measure corresponding to an extremum at the second point in time.

15. A heart test system comprising:
one or more computer processors; and
memory storing instructions for execution by the one or more computer processors, the instructions, when executed, causing the one or more computer processors to process one or more electrocardiograms acquired for a patient for one or more respective leads by performing operations comprising:
converting the one or more electrocardiograms by time-frequency transform into one or more respective two-dimensional time-frequency maps;
identifying, within the one or more electrocardiograms, points in time associated with a T wave, the points in time comprising at least a first point in time preceding the maximum of the T wave and a second point in time following the maximum of the T wave;
determining, for at least one of the one or more time-frequency maps, repolarization measures corresponding to extrema of the respective time-frequency map at the one or more points in time associated with the T wave, the repolarization measure comprising a first repolarization measure corresponding to an extremum of the respective time-frequency map at the first point in time associated with the T wave and a second repolarization measure corresponding to an extremum of the respective time-frequency map at the second point in time associated with the T wave; and
comparing the first repolarization measure with the second repolarization measure and determining a heart condition based on the comparison.

16. The system of claim 15, wherein an abnormal heart condition is determined based on the second repolarization measure being greater than the first repolarization measure.

17. The system of claim 11, wherein the electrocardiograms and respective repolarization measures include electrocardiograms and repolarization measures for at least one lead associated with a left ventricle of the patient's heart and at least one lead associated with a right ventricle of the patient's heart, the operations further comprising comparing a left ventricular repolarization index determined based on the at least one repolarization measure determined for the left ventricle with a right ventricular repolarization index determined based on the at least one repolarization measure determined for the right ventricle.

18. A heart test system comprising:
one or more computer processors; and
memory storing instructions for execution by the one or more computer processors, the instructions, when executed, causing the one or more computer processors to process electrocardiograms acquired for a patient for respective leads, including at least one electrocardiogram and respective lead associated with a left ventricle of the patient's heart and at least one electrocardiogram and respective lead associated with a right ventricle of the patient's heart, by performing operations comprising:

converting the electrocardiograms by time-frequency transform into respective two-dimensional time-frequency maps;

identifying, within electrocardiograms, one or more points in time associated with a T wave;

determining one or more repolarization measures for the left ventricle from one or more time-frequency maps computed from the at least one electrocardiogram associated with the left ventricle, and determining one or more repolarization measures for the right ventricle from one or more time-frequency maps computed from the at least one electrocardiogram associated with the right ventricle, the repolarization measures corresponding to extrema of the respective time-frequency map at the one or more points in time associated with the T wave;

comparing a left ventricular repolarization index determined based on the one or more repolarization measures determined for the left ventricle with a right ventricular repolarization index determined based on the one or more repolarization measures determined for the right ventricle; and determining an abnormal heart condition based on the right ventricular repolarization index being greater than the left ventricular repolarization index.

19. The system of claim 11, wherein the time-frequency transform comprises a continuous wavelet transform and the time-frequency map comprises a scalogram.

20. A heart test system comprising:

one or more computer processors; and memory storing instructions for execution by the one or more computer processors, the instructions, when executed, causing the one or more computer processors to process one or more electrocardiograms acquired for a patient for one or more respective leads by performing operations comprising:

converting the one or more electrocardiograms by time-frequency transform into one or more respective two-dimensional time-frequency maps;

identifying, within the one or more electrocardiograms, one or more points in time associated with a T wave;

determining, for at least one of the one or more time-frequency maps, one or more repolarization measures corresponding to extrema of the respective time-frequency map at the one or more points in time associated with the T wave; and determining a heart condition based on a comparison of at least one repolarization index determined based on the one or more repolarization measures against a threshold.

* * * * *